(12) United States Patent
Kamoda et al.

(10) Patent No.: US 6,960,681 B2
(45) Date of Patent: Nov. 1, 2005

(54) GUANIDINOMETHYL CYCLOHEXANE CARBOXYLIC ACID ESTER DERIVATIVES

(75) Inventors: Osamu Kamoda, Itami (JP); Hiromichi Fujiwara, Itami (JP); Toshiharu Yanagi, Itami (JP)

(73) Assignee: Nagase ChemteX Corporation, Osaka (JP)

( * ) Notice: Subject to any disclaimer, the term of this patent is extended or adjusted under 35 U.S.C. 154(b) by 0 days.

(21) Appl. No.: 10/623,135

(22) Filed: Jul. 18, 2003

(65) Prior Publication Data

US 2005/0075402 A1 Apr. 7, 2005

Related U.S. Application Data

(62) Division of application No. 09/721,182, filed on Nov. 22, 2000, now Pat. No. 6,831,190, which is a division of application No. 08/793,728, filed as application No. PCT/JP95/01725 on Aug. 30, 1995, now Pat. No. 6,284,791.

(30) Foreign Application Priority Data

Aug. 30, 1994 (JP) .............................. 6-243489
Aug. 30, 1994 (JP) .............................. 6-243490
Sep. 5, 1994 (JP) .............................. 6-248270
Sep. 9, 1994 (JP) .............................. 6-252655

(51) Int. Cl.$^7$ .............................. C07C 69/76

(52) U.S. Cl. ...................................... 560/59

(58) Field of Search .......................... 560/59

(56) References Cited

U.S. PATENT DOCUMENTS

| | | | |
|---|---|---|---|
| 2,584,160 A | 2/1952 | Sahyun et al. | 260/474 |
| 4,348,410 A | 9/1982 | Muramatsu et al. | 424/309 |
| 4,465,851 A | 8/1984 | Muramatsu et al. | 560/125 |
| 4,798,680 A | 1/1989 | Nohira et al. | 252/299 |
| 4,828,754 A * | 5/1989 | Takehara et al. | 252/299.65 |
| 4,844,835 A | 7/1989 | Uchida et al. | 252/299 |

FOREIGN PATENT DOCUMENTS

| | | |
|---|---|---|
| EP | 0 585 130 A2 | 2/1994 |
| FR | 2 498 183 | 7/1982 |
| GB | 2 058 773 | 4/1981 |

OTHER PUBLICATIONS

The Organic Chemistry of Drug Design and Drug Action, pp. 15–22, Silverman, 1992.
Jones et al., "Synthesis of Smectic Liquid–Crystalline Polysiloxanes from Biphenylcarboxylate Esters and Their Use as Stationary Phases for High–Resolution Gas Chromotography" Journal of Organic Chemistry, vol. 49, No. 25, 1984, pp. 4947–4951.
Kitazume et al., "Design and Synthesis of New Flourinated Ferroelectric Liquid Crystalline Ploymers" Journal of the American Chemical Society, vol. 12, No. 18, 1990, pp. 6608–6615.
Hirota et al., "Pyramidine Derivatives and Related Compounds. 39. A Novel Cycloaromatization reaction of 5–Formyl–1,3–dimethyluracil with Three–Carbon Nucleophiles. Synthesis of Subtitied 4–Hydroxybenzoates" Journal of Organic Chemistry, vol. 46, No. 20, 1981, pp. 3949–3953.
Nakajima et al., "Preparation of 3–phenylsalicylamide Derivatives" J. Pharm Soc. Japan, vol. 76, 1956, pp. 1211–1213.

* cited by examiner

*Primary Examiner*—Samuel Barts
(74) *Attorney, Agent, or Firm*—Peter F. Corless; John B. Alexander; Edwards & Angell, LLP

(57) ABSTRACT

The invention relates to novel and valuable intermediate compounds of the general formula (VIII) which can be used for the preparation of novel compounds comprising an antibacterial action, especially with a strong antibacterial action against *helicobacter pylori*, and pharmaceutically acceptable salts thereof. In the general formula (VIII) X is hydrogen or halogen, Y is hydrogen or a substituted or unsubstituted aralkyloxycarbonyl group having 8–19 carbon atoms, Z is hydrogen, a substituted aralkyloxycarbonyl group having 8–19 carbon atoms or a substituted alkoxycarbonyyl group having 2–19 carbon atoms, except that X, Y and Z are all hydrogen.

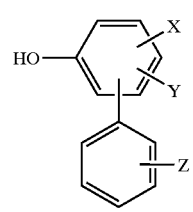

(VIII)

6 Claims, No Drawings

GUANIDINOMETHYL CYCLOHEXANE CARBOXYLIC ACID ESTER DERIVATIVES

This is a divisional application Ser. No. 09/721,182 filed on Nov. 22, 2000, now U.S. Pat. No. 6,831,190, which is a divisional of Ser. No. 08/793,728, filed on Feb. 28, 1997 which is a National Stage filing of PCT/JP95/01725, filed on Aug. 30, 1995, now U.S. Pat No. 6,284,791

FIELD OF THE INVENTION

The present invention is related to novel compounds comprising an antibacterial action, especially with a strong antibacterial action against *helicobacter pylori*, and pharmaceutically acceptable salts thereof, anti-*helicobacter pylori* agents comprising one or more compounds of the present invention, and also pharmaceutically compositions for anti-*Helicobacter pylori* comprising one or more compounds of the present invention and pharmaceutically acceptable carriers. The present invention is also related to methods of treatment for patients infected with *helicobacter pylori* comprising administration of an effective dose of one or more compounds of the invention to the patients, and usages of one or more compounds of the invention for preparation of a medicament for the treatment of *helicobacter pylori*.

BACKGROUND

*Helicobacter pylori* has been an remarked bacterium for investing lesion of a stomach and duodenum for the report by Wallen and Marshal, in Australia, in 1983 (Lancet ii: 1437–1442 (1983)). It has been known that the *helicobacter pylori* is a helicoid microaerophile gram-negative *bacillus*, adjusts its life environment by producing urease, and lives in tunica mucosa of stomach and duodenum, and also causes or recauses inflammations or ulcerations.

It was reported that the United States Public Health Research Institute presented the recommendation which means to use a combination of antiulcerative agents and antibacterial agents extermination of *helicobacter pylori* (Chem. Indust. Daily Rep. Heisei 6.7.18) because *Helicobacter pylori* is considered to be strong correlation with crisis and recurrence of peptic ulcer.

Antibiotics such as amoxicillin, cephalexin, clarislomycin (Jap. Clinic, vol. 51, No. 12, 1993), and synthetic antibacterial agents such as, ophroxacine, cyprofloxane, (APMIS, Suppl, 1007–1014, 1992) have been known as the useable compounds for extermination of *helicobacter pylori* and bacteria expulsion. Minocyline has also been known to be used for diseases caused by *helicobacter pylori*, such as gastritis (Japanese Patent Publication No. Hei 6-508635 (95/508635)).

In Japan too, while the relation between *helicobacter pylori* and peptic ulcer has been studied as the subject from now on, a movement has been raised, which investigates the corresponding to the *helicobacter pylori* has been studied with the combination of antibiotics such as amoxicillin and omeplazol, lansoplazol which comprises inhibition activity to a proton pump and are used on clinics as antiulceration agents.

Since *helicobacter pylori* is a bacterium producing urease and adjusts its life environment with the urease activity, a method for solving the above problem by using compounds with an inhibition action against the above urease activity has been known. For example, Japanese Patent Laid-Open No. 4-217950/1992 reports that aminomethylcyclohexane carboxylic acid phenyl ester group comprise the inhibition activity against the urease activity, and also inhibition action of protease, therefore it discloses useful compounds as drugs which are antiulceration agents and so on. In the above publication, a compound of which an amino group was changed to a guanidino group, or a compound shown as the following Formula (XIV) was disclosed, and reports that the above mentioned compounds showed 88.7% of ulceration restraining ratio against an ethanol hydrochloride ulceration.

XIV

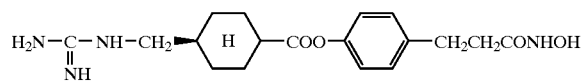

However, the above publication does not make clear about the urease inhibition activity of the compounds. Since the aim of the present invention is to provide compounds with the urease inhibition activity, it is considered that the present inventors have expected the possibility of the above mentioned compound having the urease inhibition activity.

Further, in Japanese Patent Laid-Open No. 7-118153/1995, 2-[4[(3-methoxypropoxy)-3-methylpyridine-2-ilu]methylsulfinyl-1H-benzimidazol, that is the compound shown as Formula (XV) was disclosed as a compound with the inhibition activity against urease.

XV

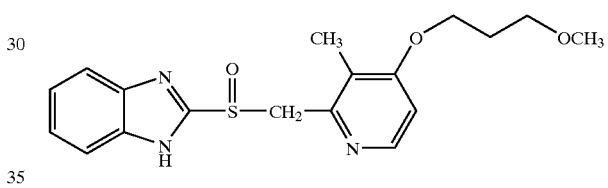

As administered antibiotics and synthetic antibacterial agents pass through digestive tract, are absorbed in intestine are metabolic-distributed among going into blood, being excreted with feces and so on, when the above drugs pass through the intestine causes extinction of many bacteria living in the intestines and casting the balance of enterobacterium. Therefore the longer-term dose of such drugs should be avoided. Accordingly, compounds which comprise selectively strong antibacterial agents against the *helicobacter pylori* have been expected.

As *hericobacter pylori* is a bacterium living in stomach, antibacterial compounds in which their antibacterial activity component acts effectively in stomachs, the antibacterial activity becomes weak as the compounds moves from duodenum to small intestines and, after all, the antibacterial activity vanishes would be expected to appear. A compound called benexarte hydrochloride has been known as a compound which has a chemical stability in stomach, and was decomposed as moving to small intestines (Progress in Medicine vol. 6, extra edition No. 1, 442 (1986)), and it is reported that the anti-*helicobacter pylori* activity of this compound was MIC 25–50 g/ml (Disease of systema digestorium and *helicobacter pylori*, P 91, Medical Review).

The present inventors took into consideration the above mentioned background and studied compounds with specific and effective antibacterial activity against *helicobacter pylori* and have achieved the present invention. And the present invention provides compounds comprising superior growth inhibition ability against *helicobacter pylori*, but do not have the activity against *esylhiacori, staphylococcus aureus*, methacycline resistant bacterium, and so on, and a characteristics which is extremely speedy decomposed by actions of decomposition enzyme in intestinum or blood.

U.S. Pat. No. 4,220,662 discloses guanidino methyl cyclohexane carboxylic acid. And as its ester body, U.S. Pat. No. 4,348,410 discloses a phenylester substituted with a group of halogen, lower alkoxy, formyl, lower alkanoylphenyl or a group of the formula —(CH2)nCOOR3 was useful for an anti-ulceration agents as a protease inhibitor, wherein R3 of said formula —(CH2)nCOOR3 is hydrogen, lower alkyl, phenyl, anisyle or alkoxycarbonylmethyl, and n is from 0 to 2. U.S. Pat. No. 4,478,995 discloses 6-benzyloxy carbonylphenyl ester was a useful antiulceration agents. Further also, it has also been well-known that such ester bodies were useful proteolytic enzyme inhibitors or antiulceration agents (Japanese Patent Publication No. 63-24988/1988, Japanese Patent Publication No. 63-24994/1988, Japanese Patent Publication No. 63-1940/1988, Japanese Patent Publication No. 63-32065/1988, Japanese Patent Publication No. 63-2255/1988, Japanese Patent Laid-Open No. 57-48960/1982, Japanese Patent Publication No. 64-2102/1989, Japanese Patent Publication No. 63-46743/1988, Japanese Patent Publication No. 64-2103/1989, Japanese Patent Publication No. 2-4588/1990, Japanese Patent Publication No. 64-2089/1989, Japanese Patent Publication No. 64-2086/1989, Japanese Patent Publication No. 64-2084/1989).

Moreover, it has also been well-known that phenyl ester which is substituted with halogen, lower alkyl, cyano, phenyl, benzyloxycarbonyl or phenoxycarbonyl group was useful to *Escherichia coli* (M. Kato et al., Biol. Pharma. Bull., 16 (2), 120–124 (1993)).

DETAILED DESCRIPTION OF THE INVENTION

The present invention is related to antibacterial agents against *helicobacter pylori* comprising guanidinomethyl cyclohexane carboxylic acid ester which is shown in the following Formula (I-1) and pharmaceutically acceptable salts thereof.

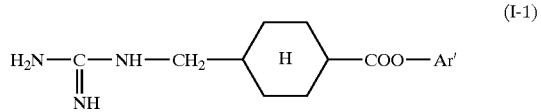
(I-1)

In the above Formula (I-1), Ar' is phenyl group, biphenyl group or naphthyl group, which has at least one substituent selected from the group consisting of halogen atom, cyano group, nitro group, carboxyl group, alkyl group having one to eighteen carbon atoms, alkoxy group having one to eighteen carbon atoms, cycloalkyl group having three to eighteen carbon atoms, aralkyl group having seven to eighteen carbon atoms, arylalkenyl group having eight to eighteen carbon atoms, aralkyloxy group having seven to eighteen carbon atoms, substituted or unsubstituted phenoxy group, substituted or unsubstituted alkoxycarbonyl group having two to nineteen carbon atoms, substituted or unsubstituted aralkyloxycarbonyl group having eight to nineteen carbon atoms.

And the present invention provides guanidinomethyl cyclohexane carboxylic acid ester shown in the following Formula (I-2) and the pharmaceutically acceptable salts thereof.

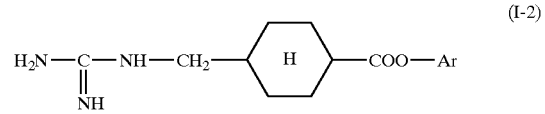
(I-2)

In the above Formula (I-2), Ar is phenyl group, biphenyl group or naphthyl group, which has at least one substituent selected from the group consisting of halogen atom, cyano group, nitro group, carboxyl group, alkyl group having one to eighteen carbon atoms, alkoxy group having one to eighteen carbon atoms, cycloalkyl group having three to eighteen carbon atoms, aralkyl group having seven to eighteen carbon atoms, arylalkenyl group having eight to eighteen carbon atoms, aralkyloxy group having seven to eighteen carbon atoms, substituted or unsubstituted phenoxy group, substituted or unsubstituted alkoxycarbonyl group having two to nineteen carbon atoms, substituted or unsubstituted aralkyloxycarbonyl group having eight to nineteen carbon atoms, with the exclusion of that Ar is phenyl group substituted with halogen, cyano, nitro, carboxyl, alkyl group having one to eighteen carbon atoms, alkoxy group having one to eighteen carbon atoms, phenoxy group, benzyloxy group, substituted or unsubstituted alkoxycarbonyl group having two to nineteen carbon atoms or aralkyloxycarbonyl group having eight to nineteen carbon atoms.

Further, the present invention provides pharmaceutical compositions for treatment of *helicobacter pylori* infective disease comprising guanidinomethyl cyclohexane carboxylic acid ester shown in the following Formula (I-2) and pharmaceutically acceptable salts thereof and pharmaceutically acceptable carriers.

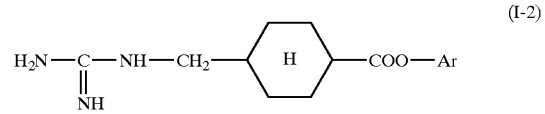
(I-2)

In the above Formula (I-2), Ar is phenyl group, biphenyl group or naphthyl group, which has at least one substituent selected from the group consisting of halogen atom, cyano group, nitro group, carboxyl group, alkyl group having one to eighteen carbon atoms, alkoxy group having one to eighteen carbon atoms, cycloalkyl group having three to eighteen carbon atoms, aralkyl group having seven to eighteen carbon atoms, arylalkenyl group having eight to eighteen carbon atoms, aralkyloxy group having seven to eighteen carbon atoms, substituted or unsubstituted phenoxy group, substituted or unsubstituted alkoxycarbonyl group having two to nineteen carbon atoms, substituted or unsubstituted aralkyloxycarbonyl group having eight to nineteen carbon atoms, with the exclusion of that Ar is phenyl group substituted with halogen, cyano, nitro, carboxyl, alkyl group having one to eighteen carbon atoms, alkoxy group having one to eighteen carbon atoms, phenoxy group, benzyloxy group, substituted or unsubstituted alkoxycarbonyl group having two to nineteen carbon atoms or aralkyloxycarbonyl group having eight to nineteen carbon atoms.

In further detail, the present invention provides compounds shown in the following Formula (I-3) or pharmaceutically acceptable salts thereof, antibacterial agents against *helicobacter pylori* comprising the above compounds of the present invention and pharmaceutical compositions of anti-*helicobacter pylori* comprising the above compounds and pharmaceutically acceptable carriers.

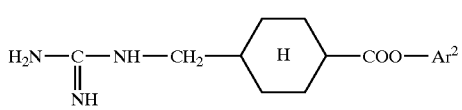
(I-3)

In the above Formula (I-3), Ar² is any group selected from the group (a) shown in the following Formula (XI), the group (b) shown in the following Formula (XII) or the group (c) shown in the following Formula (XIII).

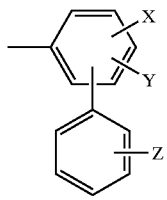
(XI)

(a) where in above Formula (XI), X and Y are selected from the group consisting of hydrogen, halogen or substituted or unsubstituted aralkyloxycarbonyl group having eight to nineteen carbon atoms respectively, Z is selected from the group consisting of hydrogen atom, halogen atom, cyano group, nitro group, carboxyl group, alkoxy group having one to eighteen carbon atoms, substituted or unsubstituted alkoxycarbonyl group having two to nineteen carbon atoms, substituted or unsubstituted aralkyloxycarbonyl group having eight to nineteen carbon atoms, except that both X and Y are not hydrogen.

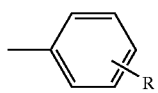
(XII)

(b) where in above Formula (XII), R is selected from the group consisting of cycloalkyl group having three to eighteen carbon atoms, aralkyl group having seven to eighteen carbon atoms, arylalkenyl group having eight to eighteen carbon atoms, aralkyloxy group having seven to eighteen carbon atoms, arylalkenyl group having eight to eighteen carbon atoms, aralkyloxy group having seven to eighteen carbon atoms or substituted or unsubstituted phenoxy group.

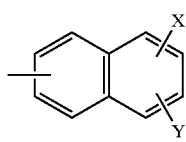
(XIII)

(c) where in above Formula (XIII), X and Y are selected from the group consisting of hydrogen, halogen or substituted or unsubstituted alkoxycarbonyl group having two to nineteen carbon atoms respectively, except that both X and Y are not hydrogen.

In further detail, the present invention provides compounds shown in the following Formula (II) or pharmaceutically acceptable salts thereof, antibacterial agents against *helicobacter pylori* comprising the above compounds of the present invention and pharmaceutical compositions of anti-*helicobacter pylori* comprising the above compounds and pharmaceutically acceptable carriers.

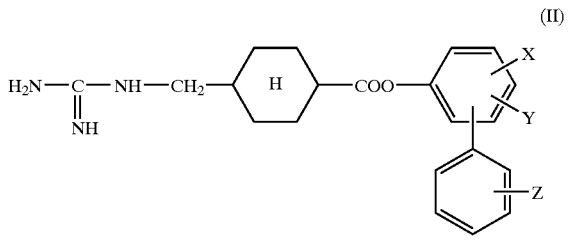
(II)

In the above Formula (II), X and Y are from the group consisting of hydrogen, halogen or substituted or unsubstituted aralkyloxycarbonyl group having eight to nineteen carbon atoms respectively, Z is selected from the group consisting of hydrogen atom, halogen atom, cyano group, nitro group, carboxyl group, alkoxy group having one to eighteen carbon atoms, substituted or unsubstituted alkoxycarbonyl group having two to nineteen carbon atoms, substituted or unsubstituted aralkyoxycarbonyl group having eight to nineteen carbon atoms, except that both X and Y are not hydrogen.

In more detail, the present invention provides compounds shown in the following Formula (III) or pharmaceutically acceptable salts thereof, antibacterial agents against *helicobacter pylori* comprising the above compounds of the present invention and pharmaceutical compositions of anti-*helicobacter pylori* comprising the above compounds and pharmaceutically acceptable carriers.

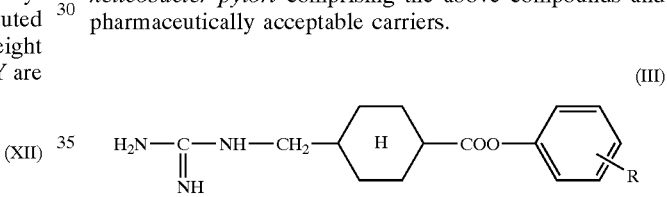
(III)

In the above Formula (III), R is selected from the group consisting of cycloalkyl group having three to eighteen carbon atoms, aralkyl group having seven to eighteen carbon atoms, arylalkenyl group having eight to eighteen carbon atoms, aralkyloxy group having seven to eighteen carbon atoms, arylalkenyl group having eight to eighteen carbon atoms, aralkyloxy group having seven to eighteen carbon atoms or substituted phenoxy group.

In more detail, the present invention provides compounds shown in the following Formula (IV) or pharmaceutically acceptable salts thereof, antibacterial agents against *helicobacter pylori* comprising the above compounds of the present invention and pharmaceutical compositions of anti-*helicobacter pylori* comprising the above compounds and pharmaceutically acceptable carriers.

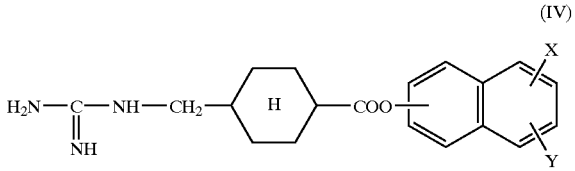
(IV)

Where in above Formula (IV), X and Y selected from the group consisting of hydrogen, halogen or substituted or unsubstituted alkoxycarbonyl group having two to nineteen carbon atoms respectively, except that both X and Y are not hydrogen.

The substituent of phenyl group, biphenyl group or naphthyl group having at least one substituent, on the guanidinomethyl cyclohexane carboxylic acid ester of the present invention and the pharmaceutically acceptable salts thereof are more detailed described by follows.

Exemplary halogen include chloride, iodine, bromide and fluorine.

As Alkyl group having one to eighteen carbon atoms, an alkyl group having from one to ten carbon atoms is preferable and one to five carbon atoms is more preferable, and these may be either linear or branching alkyl group, for example, methyl group, ethyl group, n-propyl group, i-propyl group, n-butyl group, i-butyl group, t-butyl group and so on.

As Alkoxy group having one to eighteen carbon atoms, an alkoxy group having one to ten carbon atoms is preferable and one to five carbon atoms is more preferable, and these may be either linear or branching alkoxy group, for example, methoxy group, ethoxy group, n-propoxy group and so on.

As Cycloalkyl group having three to eighteen carbon atoms, a cycloalkyl group having three to ten carbon atoms is preferable, for example, these are cyclopropyl group, cyclobutyl group, cyclohexyl group and so on.

As Aralkyl group having seven to eighteen carbon atoms, an aralkyl group having seven to ten carbon atoms is preferable, and these may be either linear or branching alkyl group, for example, benzyl group, phenethyl group and so on.

As Arylalkenyl group having eight to eighteen carbon atoms, an arylalkenyl group having eight to ten carbon atoms is preferable, and these may be either linear or branching arylalkenyl group, for example, styryl group and so on.

As Aralkyloxy group having seven to eighteen carbon atoms, an aralkyloxy group having seven to ten carbon atoms is preferable, for example, these are benzyloxy group, phenethyloxy group.

As substituents of substituted phenoxy group, e.g., halogens, cyano group, nitro group, carboxyl group, alkyl group having one to ten carbon atoms, preferably one to five carbon atoms, alkoxy group having one to ten carbon atoms, preferably one to five carbon atoms, trihalogenomethyl or alkoxycarbonyl group having two to nineteen carbon atoms, preferably two to eleven carbon atoms is suitable. And as substituted or unsubstituted phenoxy group, for example, phenoxy group, fluorophenoxy group, 4-carboxyphenoxy group, 4-methoxycarbonylphenoxy group, 4-ethoxycarbonylphenoxy group may be used.

As substituted or unsubstituted alkoxy carbonyl group having two to nineteen carbon atoms, an substituted or unsubstituted alkoxy carbonyl group having preferably two to eleven carbon atoms is suitable and it may have either linear or branching alkoxycarbonyl group. As substituents of substituted alkoxycarbonyl group, e.g., halogens, alkoxy group having one to ten carbon atoms, preferably one to five carbon atoms, cycloalkyl group having three to eighteen carbon atoms, preferably five to ten carbon atoms, halogens, and substituted or unsubstituted arlyoxy group, suitable substituents of which are, e.g., alkyl group having one to ten carbon atoms, preferably one to five carbon atoms, or alkoxy group having one to ten carbon atoms, preferably one to five carbon atoms. Exemplary alkoxycarbonyl group includes methoxycarbonyl, ethoxycarbonyl, n-propyloxycarbonyl, i-propyloxycarbonyl, cyclopropylmethyloxycarbonyl, cyclobuthylmethyloxycarbonyl, cyclohexylethyloxycarbonyl, cyclohexylmethyloxycarbonyl, cyclohexylpropyloxycarbonyl, n-buthylcyclohexylmethyloxycarbonyl, fluorophenyloxypropyloxycarbonyl.

Substituted or unsubstituted aralkyloxycarbonyl group having eight to nineteen carbon atoms indicates a substituted or unsubstituted aralkyloxycarbonyl group having preferably eight to thirteen carbon atoms, and has linear or branching alkyl group of the aralkyloxycarbonyl group. Suitable substituents of substituted aralkyloxycarbonyl group are, e.g., halogens, alkyl group having one to ten carbon atoms, preferably one to five carbon atoms, alkoxy group having one to ten carbon atoms, preferably one to five carbon atoms, trihalogenomethyl. Exemplary substituted or unsubstituted aralkyloxycarbonyl group includes benzyloxycarbonyl, fluorobenzyloxycarbonyl, chlorobenzyloxycarbonyl, ethylbenzyloxycarbonyl, methylbenzyloxycarbonyl, propylbenzyloxycarbonyl, t-buthylbenzyloxycarbonyl, methoxybenzyloxycarbonyl, trifluoromethylbenzyloxycarbonyl, dimethylbenzyloxycarbonyl, chlorophenylethyloxycarbonyl, methylphenylethyloxycarbonyl, phenylethyloxycarbonyl, phenylpropyloxycarbonyl.

As compounds of the present invention shown as the above mentioned Formula (I-1), (I-2), (I-3), (II), (III) and (IV) have nitrogen atoms respectively, the compounds of the present invention can form addition salts with various acids. These addition salts with various acids can be any salts which are the pharmaceutically acceptable salts. For example, hydrochloride, bromate, carbonate, acetate, methansulfonate, ethansulfonate, benzensulfonate, toluenesulfonate, oxalate, fumarate, coumarate, and so on can be formed. These various acid salts of the present invention can be exchanged each other, and, in this case the step via a carbonate salt is suitable.

Compounds of the present invention, or guanidinomethyl cyclohexane carboxylic acid ester shown as the below Formula (I-2) or the pharmaceutically acceptable salts thereof can be produced by the reaction between guanidinomethyl cyclohexane carboxylic acid shown as Formula (V) or the reactive derivatives thereof and the compounds shown as Formula (VI) in a suitable solvent.

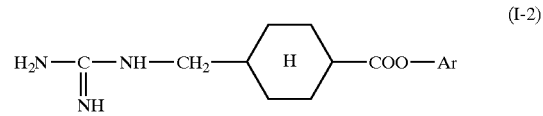

(I-2)

Where in above Formula (I-2), Ar is phenyl group, biphenyl group or naphthyl group having at least one substituent selected from the group consisting of halogens, cyano group, nitro group, carboxyl group, alkyl group having one to eighteen carbon atoms, alkoxy group having one to eighteen carbon atoms, cycloalkyl group having three to eighteen carbon atoms, aralkyl group having seven to eighteen carbon atoms, arylalkenyl group having eight to eighteen carbon atoms, aralkyloxy group having seven to eighteen carbon atoms, substituted or unsubstituted phenoxy group, substituted or unsubstituted alkoxycarbonyl group having two to nineteen carbon atoms, substituted or unsubstituted aralkyloxycarbonyl group having eight to nineteen carbon atoms, with the exclusion of that Ar is phenyl group substituted with halogens, cyano group, nitro group, carboxyl group, alkyl group having one to eighteen carbon atoms, alkoxygroup having one to eighteen carbon atoms, phenoxy group, benzyloxygroup, substituted or unsubstituted alkoxycarbonyl group having two to nineteen carbon atoms or aralkyloxycarbonyl group having eight to nineteen carbon atoms.

HO—Ar (VI)

Where in above Formula (VI), Ar is phenyl group, biphenyl group or naphthyl group having at least one substituent selected from the group consisting of halogens, cyano group, nitro group, carboxyl group, alkyl group having one to eighteen carbon atoms, alkoxy group having one to eighteen carbon atoms, cycloalkyl group having three to eighteen carbon atoms, aralkyl group having seven to eighteen carbon atoms, arylalkenyl group having eight to eighteen carbon atoms, aralkyloxy group having seven to eighteen carbon atoms, substituted or unsubstituted phenoxy group, substituted or unsubstituted alkoxycarbonyl group having two to nineteen carbon atoms, substituted or unsubstituted aralkyloxycarbonyl group having eight to nineteen carbon atoms, with the exclusion of that Ar is phenyl group substituted with halogens, cyano group, nitro group, carboxyl group, alkyl group having one to eighteen carbon atoms, alkoxy group having one to eighteen carbon atoms, phenoxy group, benzyloxy group, substituted or unsubstituted alkoxycarbonyl group having two to nineteen carbon atoms or aralkyloxycarbonyl group having eight to nineteen carbon atoms.

The suitable solvent for the above reaction can be any solvent which does not react with the starting materials. As such solvents, tetrahydrofuran, dioxane, isopropyl ether, ethylene glycol dimethyl ether, benzene, toluene, xylene, hexane, heptane, octane, petroleum ether, dichloroethane, acetonitrile, dimethylformamide, pyridine, triethylamine, dimethylaniline or mixture thereof and so on may be used.

As the derivatives when using the reactive derivative of the compound shown as Formula (V), for example, acid halide (chloride, bromide etc.), active ester (with p-nitrophenol etc.), acid anhydride, mixed acid anhydride (with ethyl chlorocarbonate, acetyl chloride, pivalic acid, $POCl_3$ etc.), and the reaction product with 1,1'-sulfinidimidazole, 1,1'-carbodiimidazole and so on may be used.

Condensation agents may be used to make react the compound having the free carboxyl group shown as Formula (V) group to the compound shown as Formula (VI). As suitable condensation agents, for example, dicyclohexylcarbodiimide, sulfuric acid, hydrogen chloride, toluensulfonic acid, thionyl chloride, phosphorus chloride, boron trifluoride and so on may be used.

Further, the reaction derivative produced from the compound shown as Formula (VI) may be make to react to the compound shown as Formula (V), or the compounds having free carboxyl group. In this case, exemplary reactive derivatives of the compound shown as Formula (VI) are, e.g., chloro sulfate derivative derived from thionylchloride, or sulfurous ester shown as Formula (VII).

Ar—O—SO—O—Ar    (VII)

(Ar of above Formula (VII) is defined the same as group Ar above mentioned.)

In more detail, compounds of the present invention, or guanidinomethyl cyclohexane carboxylic acid biphenyl ester shown as Formula (II) or the pharmaceutically acceptable acid salts thereof can be produced by the same reaction as above mentioned.

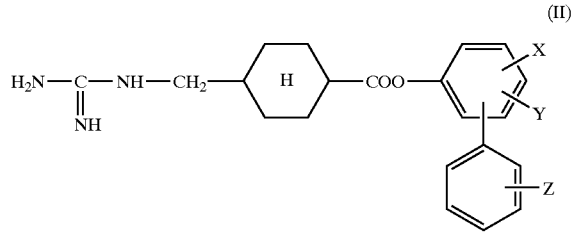

(II)

Where in above Formula (II), X and Y are selected from the group consisting of hydrogen, halogens or substituted or unsubstituted aralkyloxycarbonyl group having eight to nineteen carbon atoms respectively, Z is selected from the group consisting of hydrogen, halogens, cyano group, nitro group, carboxyl group, alkoxy group having one to eighteen carbon atoms, substituted or unsubstituted alkoxycarbonyl group having two to nineteen carbon atoms, substituted or unsubstituted aralkyoxycarbonyl group having eight to nineteen carbon atoms, except that X, Y and Z are not all hydrogen.

Namely, those compounds can be produced by the reaction between guanidinomethyl cyclohexane carboxylic acid shown as Formula (V) or the reactive derivatives thereof and the compounds shown as Formula (VIII) in a suitable solvent.

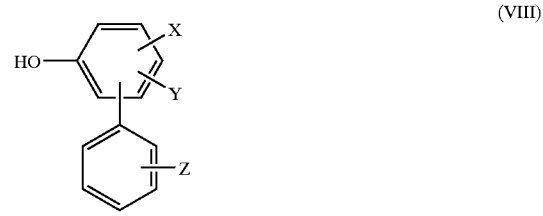

(VIII)

Where in above Formula (VIII), X and Y are selected from the group consisting of hydrogen, halogen or substituted or unsubstituted aralkyloxycarbonyl group having eight to nineteen carbon atoms respectively, Z is selected from the group consisting of hydrogen, halogens, cyano group, nitro group, carboxyl group, alkoxy group having one to eighteen carbon atoms, substituted or unsubstituted alkoxycarbonyl group having two to nineteen carbon atoms, substituted or unsubstituted aralkyloxycarbonyl group having eight to nineteen carbon atoms, except that X, Y and Z are not all hydrogen.

Conditions on the reaction, which are used solvents and reactive derivatives of the compounds shown as Formula (V) and (VIII) for the reaction, can be decided according to the above mentioned procedures and the reaction can be made the same as the above mentioned step.

Compounds of the present invention, or guanidinomethyl cyclohexane carboxylic acid phenyl ester shown as Formula (IV) or the pharmaceutically acceptable acid salts thereof can be produced by the reaction as follows.

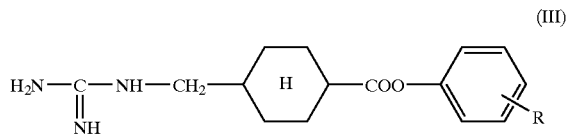

(III)

(R of said Formula (III) is defined as the same group as R above mentioned.)

Namely, those compounds can be produced by the reaction between guanidinomethyl cyclohexane carboxylic acid shown as Formula (V) or the reactive derivatives thereof and the compounds shown as Formula (IX) in a suitable solvent.

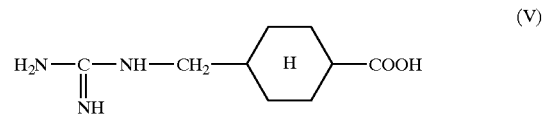

(V)

(R of said Formula (V) is defined as the same group as R above mentioned.)

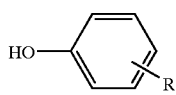

(R of said Formula (IX) is defined as the same group as R above mentioned.)

Conditions on the reaction, which are used solvents and reactive derivatives of the compounds shown as Formula (V) and (IX) for the reaction, can be decided according to the above mentioned procedures and the reaction can be made the same as the above mentioned step.

Compounds of the present invention, or guanidinomethyl cyclohexane carboxylic acid naphthyl ester shown as Formula (IV), or the pharmaceutically acceptable salts thereof can be produced by the reaction between guanidinomethyl cyclohexane carboxylic acid shown as Formula (V) or the reactive derivatives thereof and the compounds shown as Formula (IV) in a suitable solvent.

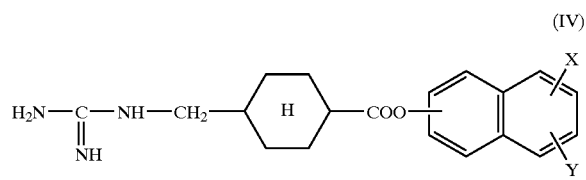

Where in said Formula (IV), X and Y are selected from the group consisting of hydrogen, halogen or substituted or unsubstituted alkoxycarbonyl group having two to nineteen carbon atoms respectively, except that both X and Y are not hydrogen.

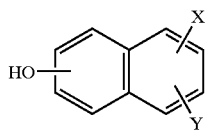

Where in said Formula (X), X and Y are selected from the group consisting of hydrogen, halogen or substituted or unsubstituted alkoxycarbonyl group having two to nineteen carbon atoms respectably, except that both X and Y are not hydrogen.

Conditions on the reaction, which are used solvents and reactive derivatives of the compounds shown as Formula (V) and (X) for the reaction, can be decided according to the above mentioned procedure and the reaction can be made the same as the above mentioned step.

Moreover, in the above Formula (II) and (VIII), substituting positions of the benzene ring having substituent Z can be any position of ortho, meta and para. In the above Formula (IX), bonding position between COO— and naphthyl group is the first position or the second position of the naphthyl group. And positions of substituents X and Y can be any of remained positions of the naphthyl group.

And as compounds shown as Formula (V) used as starting materials also include acid addition salts, these acid addition salts are the same as the above mentioned pharmaceutically acceptable salts.

As compounds shown as Formula (I-1), (I-2), (I-3), (II), (III), (IV) include cyclohexane ring respectively, guanidinomethyl group thereof and carbonyl group thereof can be bonded with the trans type and the cis type at ends of the cyclohexane ring, and the above mentioned compounds of the present invention and the pharmaceutically acceptable salts thereof also include these both types of compounds, preferred is the trans type. This geometrical isomer depends on that of compound shown as Formula (V) which are used as a starting material.

And the present invention also relates to methods of treatment for patients infected with *helicobacter* pylon comprising administration of an effective dose of one or more compounds of the present invention to the patients, and uses of one or more compounds of the present invention for preparing treatment agents thereof.

The oral administration dose of the antibacterial agents of the present invention, which is decided according to patients and symptoms, may be 10–200 mg/dose, and according to symptoms the agents can be administered two or three time per day. On the occasion, pharmaceutical forms thereof may be any form which can be oral-administered, exemplary includes tablets, pellets, powder, granules, capsules, dry syrup or other solutions. For example, those preparation can be prepared with referring to the description at the pharmaceutical general rules in the Japanese Pharmacopoeia.

The excipients for obtaining solid preparations may be exemplary saccharide, such as saccharose, milk sugar, mannitol, glucose, starch and starch derivatives, crystal cellulose, low-substitutional hydroxy propylcellulose, calcium hydrogenphosphate, calcium sulfate calcium lactate, calcium citrate, sucrose aliphatic ester, polyoxyethylene-polyoxypropyleneglycol group and so on. The decay agents may be such as starch, calcium carbonate, carmelose and the salts thereof, and so on. And the binding agents may be such as polyvinylalcohol, polyvinylpyrrolidone, hydroxyethylcellulose, hydroxypropylmethylcellulose, hydroxypropylcellulose, macrogol group, gum arabic, gelatin, starch and so on. The glossing agents may be such as tarc, magnesium stearate, calcium stearate, colloidal silica, stearic acid, wax group, hardemed oil, polyethyleneglycol group and so on.

The solution agent for preparing suspension agents, such as lyophobic agents, exemplary include gum arabic, gum xanthene, gelatin, sodium alaginic acid, Borbitol, glycerin, cane sugar or cellulose derivatives, such as sodium carmelose, methylcellulose and so on. And the preservative agents may be such as benzoic acid, paraoxy benzoic acid ester group and so on.

And the edulcorrant agents may be such as saccharose, sodiumsaccharine, sorbitol and so on. And the flavor agents may be such as citric acid, peppermint oil, eucally oil and so on.

The antibacterial action of the compounds of the present invention are examined as follows.

1. Minimum Inhibitory Concentration (MIC) was measured in accordance with the standard method of Japanese Chemotherapy Academy (Chemotherapy, 29: 76–79, 1981).

1) Measuring Methods of Sensitivity

Sensitivity was measured with an agar plating dilution using Brain-Heart Infusion agar (Difco Co.) which was added 0.1% of cyclodextrin.

2) Concentration Stepwise of Antibacterial Agents

The prepared concentration stepwise were 25, 12.5, 6.25, 3.13, 1.56, 0.78, 0.39, 0.20, 0.10, 0.05, 0.025 and 0.0125 g/ml.

10,000 g/ml of the solutions of the compounds which were obtained in examples of the present invention was prepared by dissolving in dimethylsulfoxide. The solution was diluted with sterilized distilled water to 250, 125, 62.5, 31.3, 15.6, 7.8, 3.9, 2.0, 1.0, 0.5, 0.25 and 0.125 g/ml. Each of 1 ml of those prepared solutions was dispensed in share, after sterilization, 9 ml of sensitivity measuring medium which is kept at 50° C. was added to each, and they were sufficiently mixed. The mixture was used as a plate for measuring sensitivity.

3) Bacterial Solution for Inoculation

Brain Heart Infusion agar medium (Difco Co.), which was added 0.1% of cyclodextrin, was used as bacteria growing medium, and was cultured under microair at 37° C. for three days, and the number of bacteria thereof was adjusted to about 106/ml. This was used as a bacterial solution for inoculation.

4) Method of Inoculating Bacteria

The medium was painted in each square about 2 cm with nichromic line loop.

5) Period and Temperature of the Culture

The medium was cultured under microair for three days at 37° C.

6) Evaluation

Minimum concentration which was completely inhibit growth of the medium was judged as the value of MIC.

2. Minimum Inhibitory Concentration (MIC) and Minimum Bacteria Sterilizeory

Concentration (MBC) against *helicobacter* pylon were measured in accordance with the liquid medium dilution.

1,000 g/ml of the solution of the compounds which were obtained in examples of the present invention was prepared by dissolving in dimethylsulfoxide (DMSO), and distilled water was added to the solutions to prepare double dilution system (200, 100, . . . , 0.05 g/ml). 1 ml of Brain-Heart Infusion broth (Difco Co.) which was added 0.1% of -cyclo dextrin and then was prepared at double concentration, was added to each of 1 ml of those above DMSO solutions and mixed. And 10 I of *helicobacter* pylon bacterial solution, which was cultured at 37° C. for three days and then diluted and prepared with the above mentioned liquid medium, was added to the mixtures to adjust the volume to 105 CFU/ml. The mixture was cultured in a multi-gas incubator (10% $CO_2$, 5% $O_2$, 85% $N_2$) at 37° C. for three days and minimum concentration of the compounds which were not recognized the growth with the naked eyes were measured as the values of MIC.

After the evaluation of MIC, each 100 I of the compounds in each test tube was added to 4 ml of new liquid medium respectively. After they were cultured by the same method as above mentioned, minimum concentration of the compounds which were not recognized the growth with the naked eyes were measured as the values of MBC.

The present invention will be described more specifically with several examples. The following examples do not limit the present invention.

4. Best Modes of Operation of the Invention

As comparative samples, the minimum inhibitory concentration (MIC) of the following well-known compounds other than compounds of examples were measured by the same procedure as above mentioned.

Compound 1: trans-4-guanidinomethyl cyclohexane carboxylic acid (4-phenylphenylester)hydrochloride Compound 2: trans-4-guanidinomethyl cyclohexane carboxylic acid (2-phenylphenylester)hydrochloride Compound 3: trans-4-guanidinomethyl cyclohexane carboxylic acid (1-naphthylester)hydrochloride Compound 4: trans-4-guanidinomethyl cyclohexane carboxylic acid (2-naphthylester)hydrochloride While Compounds 5, 6 and 7 are well known as protease inhibitors, those compounds unexpectedly have antimicrobial activity against *helicobacter pylori*. Therefore they were used as the compounds for comparative examples.

Each of those compounds are shown below.

Compound 5:

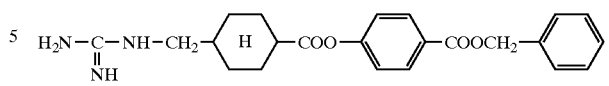

Compound 6:

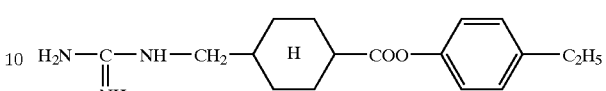

Compound 7:

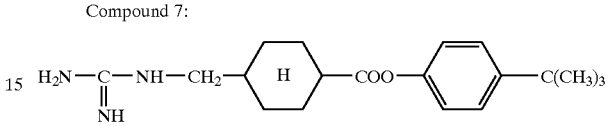

The values of MIC of the compounds obtained in Examples 1–27 and Compounds 1 and 2 were shown at Table 1, the values of MIC of the compounds of Examples 29–31 and Compounds 3 and 4 were shown at Table 2, the values of MIC of the compounds of Examples 32–38 and Compounds 5–7 were shown at Table 3, and the values of MIC of the compounds of Examples 37–46 were shown at Table 6.

As a comparison, MICs of ophroxacine and amoxicillin were measured and the results were shown at Table 1, 3, 6 and 7. And, in the compounds of Example 1–38 and Compounds 1–7, each antibacterial activity against *Escherichia coli*. were also measured in accordance with the standard method of Japanese Chemotherapy Academy. The results were shown at corresponding tables respectively.

The antibacterial activities of the compounds of Compounds 1 and Example 4 were measured using the medium with 7% horse's defiber blood, which is the product been on the market, instead of 0.1% -cyclodextorin used as the sensivity of measuring medium for the measurement of antibacterial activity. As the results, the values of MIC were >25 g/ml and >25 g/ml respectively.

For reference, the value of MIC of benexart hydrochloride was >100 g/ml.

Moreover, each value of MBC of the compounds of Examples 2, 3, 8, 14–21, 23–26 and Compound 1 against clinical segregation strains was measured in accordance with the above mentioned method. The each result is shown at Table 4.

Further more, MIC and MBC of the compounds of Example 14, 15 and 16 were measured using the liquid medium, and the results are shown at Table 5.

And MIC of the compounds of Example 3, 36, 8, 14, 17, 21, 41 and 45 were measured. The results were shown at Table 7.

EXAMPLE 1

Cooling down with ice, 1.67 g of thionyl chloride was added by dropping to a mixture of 3-phenylphenol 4.77 g, pyridine 2.21 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 3.00 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration and they were washed with acetone. 3.58 g of trans-4-guanidinomethyl cyclohexane carboxylic acid(3-phenylphenylester)·hydrochloride was obtained.

mp 131–133° C.; NMR (DMSO-$d_6$) δ 0.8–3.3 (12H,m), 6.8–8.2 (14H,m)

EXAMPLE 2

Cooling down with ice, 0.98 g of thionyl chloride was added by dropping to a mixture of 4-(4-hydroxyphenyl)ethyl benzoate 4.00 g, pyridine 1.31 g and dried tetrahydrofuran 30 ml. After the mixture was stirred for 3 hours at room temperature, and precipitated crystals were collected by filtration. The filtrate was concentrated under reduced pressure and crystals were obtained. 30 ml of dried pyridine was added to the crystals and the mixture was cooled down with ice. And 1.77 g of trans-4-guanidinomethyl cyclohexane carboxylic acid.hydrochloride was added to the cooled mixture. After stirring this mixture during night at room temperature, the mixture was concentrated under reduced pressure. After acetone was added to the residue, and precipitated crystals were collected by filtration. And they were washed with acetone, and 3.98 g of crude crystals were collected. They were purified by recrystallization from ethanol. 2.57 g of trans-4-guanidinomethyl cyclohexane carboxylic acid [4-(4-ethoxycarbonylphenyl)phenylester]·hydrochloride was obtained.

mp 211–213° C. NMR (DMSO-$d_6$) δ 0.8–3.3 (12H,m), 6.8–8.2 (14H,m)

EXAMPLE 3

Cooling down with ice, 1.11 g of thionyl chloride was added by dropping to a mixture of 4-(4-hydroxyphenyl) benzyl benzoate 5.68 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, precipitated crystals were collected by filtration and they were washed with acetone. 3.95 g of trans-4-guanidinomethyl cyclohexane carboxylic acid [4-(4-benzyloxycarbonylphenyl)phenylester]·hydrochloride was obtained.

mp 198–201° C.; NMR (DMSO-$d_6$) δ 0.8–3.3 (12H,m), 5.41 (2H,s), 7.0–8.3 (18H,m)

The value of MIC against bacillus subcillus ATCC 6633 measured in accordance with the standard method of Japanese Chemotherapy Academy was >25 g/ml.

EXAMPLE 4

Cooling down with ice, 1.67 g of thionyl chloride was added by dropping to a mixture of 4-(4-bromophenyl)phenol 6.98 g, pyridine 2.21 g and dried tetrahydrofuran 50 ml. After the mixture was stirred for 4 hours at room temperature, and precipitated crystals were collected by filtration. The filtrate was concentrated under reduced pressure and crystals were obtained. 30 ml of dried pyridine was added to the crystals and the mixture was cooled down with ice. And 3.00 g of trans-4-guanidinomethylcyclohexane carboxylic acid hydrochloride was added to the cooled mixture. After stirring this mixture during night at room temperature, the mixture was concentrated under reduced pressure. After acetone was added to the residue, precipitated crystals were collected by filtration. And they were washed with acetone, and 5.90 g of the crude crystals were collected. The crude crystals were dispersed with 50 ml of ethanol, collected by filtration, and were washed in order with ethanol and acetone. 5.67 g of trans-4-guanidinomethyl cyclohexane carboxylic acid [4-(4-bromophenyl)phenylester]·hydrochloride was obtained.

mp 233–235° C.; NMR (DMSO-$d_6$) δ 0.7–3.2 (12H,m), 7.0–8.2 (13H,m)

EXAMPLE 5

Cooling down with ice, 0.89 g of thionyl chloride was added by dropping to a mixture of 4-(4-methoxyphenyl)phenol 3.00 g, pyridine 1.19 g and dried tetrahydrofuran 50 ml. After the mixture was stirred for 4 hours at room temperature, and precipitated crystals were collected by filtration. The filtrate was concentrated under reduced pressure and an oily product was obtained. 30 ml of dried pyridine was added to the oily product and the mixed oily product was cooled down with ice. And 1.61 g of trans-4-guanidinomethyl cyclohexane carboxylic acid·hydrochloride was added to the cooled mixture. After stirring this mixture during night at room temperature, the mixed oily product was concentrated under reduced pressure. After acetone was added to the residue, precipitated crystals were collected by filtration, and they were washed with acetone. 2.44 g of trans-4-guanidinomethyl cyclohexane carboxylic acid [4-(4-methoxyphenyl)phenylester]·hydrochloride was obtained.

mp 217–220° C.; NMR (DMSO-$d_6$) δ 0.8–3.3 (12H,m), 3.80 (3H,s), 6.7–8.2 (13H,m)

EXAMPLE 6

Cooling down with ice, 1.67 g of thionyl chloride was added by dropping to a mixture of 2-chloro-4-phenylphenol 5.73 g, pyridine 2.22 g and dried tetrahydrofuran 50 ml. After the mixture was stirred for 4 hours at room temperature, precipitated crystals were collected by filtration. The filtrate was concentrated under reduced pressure and oily product was obtained. 30 ml of dried pyridine was added to the oily product and the mixed oily product was cooled down with ice. And 3.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, the precipitated crystals were collected by filtration, and they were washed with acetone. 5.30 g of trans-4-guanidinomethyl cyclohexane carboxylic acid (2-chloro-4-phenylphenylester)·hydrochloride was obtained.

mp 186–188° C.; NMR (DMSO-$d_6$) δ 0.8–3.3 (12H,m), 7.0–7.9 (12H,m), 8.07 (1H,bt)

EXAMPLE 7

Cooling down with ice, 1.11 g of thionyl chloride was added by dropping to a mixture of 4-(4-cyanophenyl)phenol 3.64 g, pyridine 1.48 g and dried tetrahydrofuran 50 ml. After the mixture was stirred for 4 hours at room temperature, and precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixed oily product was concentrated under reduced pressure. After acetone was added to the residue, precipitated crystals were collected by filtration, and they were washed with acetone. 3.17 g of trans-4-guanidinomethyl cyclohexane carboxylic acid [4-(4-cyanophenyl)phenylester] ·hydrochloride was obtained.

mp 207–209° C.; NMR (DMSO-$d_6$) δ 0.8–3.4 (12H,m), 7.1–8.3 (13H,m)

EXAMPLE 8

Cooling down with ice, 0.15 g of thionyl chloride was added by dropping to a mixture of 4-(4-chlorophenyl)phenol 0.50 g, pyridine 0.19 g and dried tetrahydrofuran 20 ml. After the mixture was stirred for 4 hours at room temperature, precipitated crystals were collected by filtration. The filtrate was concentrated under reduced pressure and an oily product was obtained. 20 ml of dried pyridine was added to the oily product and the mixed oily product was cooled down with ice. And 0.26 g of trans-4-guanidinomethylcyclohexane carboxylic acid hydrochloride was added to the cooled mixture. After stirring this mixture during night at room temperature, the mixed oily product was concentrated under reduced pressure. After acetone was added to the residue, precipitated crystals were collected by filtration, and they were washed with acetone. 0.43 g of trans-4-guanidinomethyl cyclohexane carboxylic acid [4-(4-chlorophenyl)phenylester]·hydrochloride was obtained.

mp 218–220° C.; NMR (DMSO-$d_6$) δ 0.7–3.2 (12H,m), 6.9–8.2 (13H,m)

EXAMPLE 9

Cooling down with ice, 1.44 g of thionyl chloride was added by dropping to a mixture of 3-phenylsalicylate benzylester 7.00 g, dried pyridine 1.92 g and dried tetrahydrofuran 30 ml. After the mixture was stirred for 3 hours at room temperature, precipitated crystals were collected by filtration. The filtrate was concentrated under reduced pressure and oily product was obtained. 30 ml of dried pyridine was added to the oily product and the mixed oily product was cooled down with ice. And 2.46 g of trans-4-guanidinomethyl cyclohexane carboxylic acid·hydrochloride was added to the cooled mixture. After stirring this mixture during night cooling down with ice, the mixture was concentrated under reduced pressure and acetone was added to them, and stirred. Its supernatant was removed by decantation and acetone was added again. The solution was stirred during night, and precipitated crystals were collected by filtration, and washed with acetone. 2.13 g of trans-4-guanidinomethyl cyclohexane carboxylic acid (2-benzyloxycarbonyl-6-phenylphenylester)·hydrochloride was obtained.

mp 81–85° C.; NMR (DMSO-$d_6$) δ 0.6–3.2 (12H,m), 5.28 (2H,s), 6.7–8.2 (18H,m)

EXAMPLE 10

Cooling down with ice, 0.56 g of thionyl chloride was added by dropping to a mixture of 3-phenylsalicylate(4-fluorobenzylester) 3.01 g, pyridine 0.74 g and dried tetrahydrofuran 20 ml. After the mixture was stirred for 3 hours at room temperature, precipitated crystals were collected by filtration. The filtrate was concentrated under reduced pressure and oily product was obtained. 20 ml of dried pyridine was added to the oily product and the mixed oily product was cooled down with ice. And 1.00 g of trans-4-guanidinomethyl cyclohexane carboxylic acid·hydrochloride was added to the cooled mixture. After stirring this mixture during night cooling down with ice, the mixed oily product was concentrated under reduced pressure. After isopropyl ether was added to the residue and stirred, the supernatant was removed by decantation. 80 ml of water was added to the solution, and 0.45 g of potassium hydrogencarbonate was added cooling down with ice, and stirred during night cooling down with ice. After 80 ml of ethanol was added to the solution cooling down with ice, precipitated crystals were collected by filtration, and washed in order with water, ethanol and acetone. 0.45 g of carbonate was obtained, and the carbonate was added into methanol. 0.08 g of methanesulfonic acid was added to the mixture cooling down with ice and concentrated under reduced pressure. After acetone was added to the residue and stirred, precipitated crystals were collected by filtration. 0.42 g of trans-4-guanidinomethyl cyclohexane carboxylic acid [2-(4-fluorobenzyloxycarbonyl)-6-phenylphenyl ester] ·methansulfonate was obtained.

mp 198–200° C.; NMR (DMSO-$d_6$) δ 0.5–3.2 (12H,m), 2.48 (3H,s), 5.28 (2H,s), 6.6–7.8 (15H,m), 7.92 (1H,d), 8.04 (1H,d)

EXAMPLE 11

Cooling down with ice, a mixture of trans-4-guanidinomethyl cyclohexane carboxylic acid·hydrochloride 1.80 g, 5-bromo-3-phenylsalicylate(4-fluorobenzylester) 3.37 g and pyridine 30 ml was stirred. After 1.73 g of N,N'-dicyclohexylcarbodiimido was added to the mixture, the mixture was stirred during night at room temperature. Precipitated crystals were collected by filtration, and the filtrate was concentrated under reduced pressure. 30 ml of water was added to the residue, and 0.80 g of potassium hydrogen carbonate was added cooling down with ice. After 80 ml of ethanol was added to the solution cooling down with ice, precipitated crystals were collected by filtration, and washed in order with water, ethanol and acetone. 3.79 g of carbonate was obtained. 0.69 g of the carbonate was added into methanol, and 0.12 g of methanesulfonic acid was added to the mixture cooled down with ice. Some insoluble substances were filtered, and the filtrate was concentrated under reduced pressure. After acetone was added to the residue and stirred, precipitated crystals were collected by filtration. They were washed with acetone and 0.36 g of crude crystals were collected. The crude crystals were dispersed by isopropanol, collected by filtration, and washed with isopropanol. 0.22 g of trans-4-guanidinomethyl cyclohexane carboxylic acid[4-bromo-2-(4-fluorobenzyloxycarbonyl)-6-phenylphenylester] .methanosulfonate was obtained.

mp 206–208° C.; NMR (DMSO-$d_6$) δ 0.5–3.2 (12H,m), 2.48 (3H,s), 5.31 (2H,s), 6.5–7.7 (14H,m), 7.81 (1H,d), 8.09 (1H,d)

EXAMPLE 12

Cooling down with ice, 0.67 g of thionyl chloride was added by dropping to a mixture of 2,4-dichloro-6-phenylphenol 2.68 g, pyridine 0.89 g and dried tetrahydrofuran 20 ml. After the mixture was stirred for 3 hours at room temperature, precipitated crystals were collected by filtration. The filtrate was concentrated under reduced pressure. 20 ml of dried pyridine was added to the residue, and the mixture was cooled down with ice. After acetone was added to them, the supernatant was removed by decantation and acetone was added again. The solution was stirred and precipitated crystals were collected by filtration, and washed with acetone. The precipitated crystals were collected filtration, and washed with acetone. The crude crystals were dispersed into isopropanol, collected by filtration, and washed with isopropanol. 0.39 g of trans-4-guanidinomethyl cyclohexane carboxylic acid (2,4-dicloro-6-phenylphenyl ester)·hydrochloride was obtained.

mp 199–200° C.; NMR (DMSO-$d_6$) δ 0.7–3.2 (12H,m), 6.9–8.1 (12H,m)

EXAMPLE 13

Cooling down with ice, 0.59 g of thionyl chloride was added by dropping to a mixture of 2,6-dichloro-4-phenylphenol 2.37 g, dried pyridine 0.78 g and dried tetrahydrofuran 20 ml. After the mixture was stirred for 3 hours at room temperature, precipitated crystals were collected by filtration. The filtrate was concentrated under reduced pressure. 20 ml of dried pyridine was added to the residue cooling down with ice. And 1.06 g of trans-4-guanidinomethyl cyclohexane carboxylic acid·hydrochloride was added to the cooled mixture. After stirring this mixture during night cooling down with water, the mixture was concentrated under reduced pressure. Acetone was added to it and stirred, and precipitated crystals were collected by filtration and washed with acetone. The crude crystals were dispersed into isopropanol, collected by filtration, and washed with isopropanol. 0.35 g of trans-4-guanidinomethyl cyclohexane carboxylic acid (2,6-dichloro-4-phenylphenylester)·hydrochloride was obtained.

mp 169–173° C.; NMR (DMSO-$d_6$) δ 0.7–3.2 (12H,m), 6.9–8.1 (12H,m)

EXAMPLE 14

Cooling down with ice, 1.11 g of thionyl chloride was added by dropping to a mixture of 4-(4-hydroxyphenyl)benzoate(4-methylbenzylester) 5.95 g, pyridine 1.48 g and dried tetrahydrofuran 30 ml. After the mixture was stirred for 3 hours at room temperature, precipitated crystals were collected by filtration. The filtrate was concentrated under reduced pressure. 30 ml of dried pyridine was added to the residue and the mixed residue was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, precipitated crystals were collected by filtration, and they were washed with acetone. The crystals were dispersed into isopropanol, collected by filtration, and washed with isopropanol. 3.19 g of trans-4-guanidinomethyl cyclohexane carboxylic acid[4-[4-(4-methylbenzyloxy carbonyl)phenyl]phenylester]·hydrochloride was obtained.

mp 171–173° C.; NMR (DMSO-$d_6$) δ 0.6–3.3 (12H,m), 2.31 (3H,s), 5.30 (2H,s), 6.7–8.4 (17H,m)

The value of MIC against *bacillus subcillus* ATCC 6633 measured in accordance with the standard method of Japanese Chemotherapy Academy was >25 g/ml.

EXAMPLE 15

Cooling down with ice, 1.11 g of thionyl chloride was added by dropping to a mixture of 4-(4-hydroxyphenyl)benzoate(4-chlorobenzylester) 6.35 g, pyridine 1.48 g and dried tetrahydrofuran 30 ml. After the mixture was stirred for 3 hours at room temperature, precipitated crystals were collected by filtration. The filtrate was concentrated under reduced pressure. 30 ml of dried pyridine was added to the residue and the mixture was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, precipitated crystals were collected by filtration, and they were washed with acetone. The crude crystals were dispersed into isopropanol, collected by filtration, and washed with isopropanol. 1.08 g of trans-4-guanidinomethyl cyclohexane carboxylic acid [4-[4-(4-chlorobenzyloxy carbonyl)phenyl]phenylester]·hydrochloride was obtained.

mp 179–182° C.; NMR (DMSO-$d_6$) δ 0.6–3.3 (12H,m), 5.34 (2H,s), 6.7–8.5 (17H,m)

The value of MIC against *bacillus subcillus* ATCC 6633 measured in accordance with the standard method of Japanese Chemotherapy Academy was >25 g/ml.

EXAMPLE 16

Cooling down with ice, 1.11 g of thionyl chloride was added by dropping to a mixture of 4-(4-hydroxyphenyl)benzoate(4-fluorobenzylester) 6.02 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, and precipitated crystals were collected by filtration, and they were washed with acetone. The crystals were dispersed into isopropanol, collected by filtration, and washed with isopropanol. 3.22 g of trans-4-guanidinomethyl cyclohexane carboxylic acid [4-[4-(4-fluorobenzyloxycarbonyl)phenyl]phenylester]·hydrochloride was obtained.

mp 178–180° C.; NMR (DMSO-$d_6$) δ 0.7–3.3 (12H,m), 5.36 (2H,s), 6.8–8.6 (17H,m)

The value of MIC against *bacillus subcillus* ATCC 6633 measured in accordance with the standard method of Japanese Chemotherapy Academy was 25 g/ml.

EXAMPLE 17

Cooling down with ice, 1.11 g of thionyl chloride was added by dropping to a mixture of 4-(4-hydroxyphenyl)benzoate(4-t-butylbenzylester) 6.73 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, and the precipitated crystals were collected by filtration, and they were washed with acetone. The crude crystals were dispersed into isopropanol, collected by filtration, and washed with isopropanol. 1.81 g of trans-4-guanidinomethyl cyclohexane carboxylic acid [4-[4-(4-t-butylbenzyloxy carbonyl)phenyl]phenylester]·hydrochloride was obtained.

mp 186–187° C.; NMR (DMSO-$d_6$) δ 0.7–3.3 (21H,m), 5.36 (2H,s), 6.8–8.5 (17H,m)

The value of MIC against *bacillus subcillus* ATCC 6633 measured in accordance with the standard method of Japanese Chemotherapy Academy was >25 g/ml.

EXAMPLE 18

Cooling down with ice, 1.11 g of thionyl chloride was added by dropping to a mixture of 4-(4-hydroxyphenyl)benzoate(4-methoxybenzylester) 6.25 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, and precipitated crystals were collected by filtration, and they were washed with acetone. The crude crystals were dispersed into isopropanol, collected by filtration, and washed with isopropanol. 3.62 g of trans-4-guanidinomethyl cyclohexane carboxylic acid [4-[4-(4-methoxybenzyloxy carbonyl)phenyl]phenylester]·hydrochloride was obtained.

mp 180–183° C.; NMR (DMSO-$d_6$) δ 0.6–3.4 (12H,m), 3.75 (3H,s), 5.30 (2H,s), 6.7–8.5 (17H,m)

The value of MIC against *bacillus subcillus* ATCC 6633 measured in accordance with the standard method of Japanese Chemotherapy Academy was 25 g/ml.

EXAMPLE 19

Cooling down with ice, 1.11 g of thionyl chloride was added by dropping to a mixture of 4-(4-hydroxyphenyl)benzoate(2-fluorobenzylester) 6.03 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, and precipitated crystals were collected by filtration, and were washed with acetone. The crude crystals were dispersed into isopropanol, collected by filtration, and washed with isopropanol. 2.93 g of trans-4-guanidinomethyl cyclohexane carboxylic acid [4-[4-(2-fluorobenzyloxycarbonyl)phenyl]phenylester]·hydrochloride was obtained.

mp 180–183° C.; NMR (DMSO-$d_6$) δ 0.6–3.3 (12H,m), 5.45 (2H,s), 6.8–8.5 (17H,m)

The value of MIC against *bacillus subcillus* ATCC 6633 measured in accordance with the standard method of Japanese Chemotherapy Academy was >25 g/ml.

EXAMPLE 20

Cooling down with ice, 1.11 g of thionyl chloride was added by dropping to a mixture of 4-(4-hydroxyphenyl)benzoate isopropylester 4.80 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, and precipitated crystals were collected by filtration, and they were washed with acetone. 2.07 g of trans-4-guanidinomethyl cyclohexane carboxylic acid [4-(4-isopropyloxycarbonyl)phenylphenylester]·hydrochloride was obtained.

mp 188–190° C.; NMR (DMSO-$d_6$) δ 0.6–3.3 (18H,m), 5.20 (1H,quin), 6.8–8.5 (13H,m)

EXAMPLE 21

Cooling down with ice, 1.11 g of thionyl chloride was added by dropping to a mixture of 4-(4-hydroxyphenyl)benzoate(4-trifuluoromethyl benzylester) 6.95 g, pyridine 1.48 g and dried tetrahydrofuran 50 ml. After the mixture was stirred for 4 hours at room temperature, precipitated crystals were collected by filtration. The filtrate was concentrated under reduced pressure and an oily product was obtained. 30 ml of dried pyridine was added to the oily product and the mixed oily product was cooled down with ice. And 2.00 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, and precipitated crystals were collected by filtration, and they were washed with acetone. The crude crystals were dispersed into isopropanol, collected by filtration, and washed with isopropanol. 3.20 g of trans-4-guanidinomethyl cyclohexane carboxylic acid [4-[4-(4-trifuluoromethyl benzyloxycarbonyl)phenyl]phenylester]·hydrochloride was obtained.

mp 188–190° C.; NMR (DMSO-$d_6$) δ 0.6–3.4 (12H,m), 5.50 (2H,s), 6.9–8.5 (17H,m)

The value of MIC against *bacillus subcillus* ATCC 6633 measured in accordance with the standard method of Japanese Chemotherapy Academy was >25 g/ml.

EXAMPLE 22

Cooling down with ice, 0.14 g of thionyl chloride was added by dropping to a mixture of 4-(4-nitrophenyl)phenol 0.50 g, dried pyridine 0.18 g and dried tetrahydrofuran 5 ml. After the mixture was stirred for 3 hours at room temperature, precipitated crystals were collected by filtration. The filtrate was concentrated under reduced pressure. 5 ml of dried pyridine was added to the residue and the mixture was cooled down with ice. And 0.25 g of trans-4-guanidinomethyl cyclohexane carboxylic acid·hydrochloride was added to the cooled mixture. After stirring this mixture during night cooling down with ice, the mixture was concentrated under reduced pressure. After acetone was added to the residue, precipitated crystals were collected by filtration, and washed with acetone. The crude crystals were dispersed into isopropanol, collected by filtration, and washed with isopropanol. 0.12 g of trans-4-guanidinomethyl cyclohexane carboxylic acid [4-(4-nitrophenyl)phenylester]·hydrochloride was obtained.

mp 174–177° C.; NMR (DMSO-$d_6$) δ 0.7–3.2 (12H,m), 6.8–8.7 (13H,m)

EXAMPLE 23

Cooling down with ice, 0.83 g of thionyl chloride was added by dropping to a mixture of 4-(4-hydroxyphenyl) benzoate cyclohexylmethylester 4.35 g, dried pyridine 1.11 g and dried tetrahydrofuran 30 ml. After the mixture was stirred for 3 hours at room temperature, precipitated crystals were collected by filtration. The filtrate was concentrated under reduced pressure. 30 ml of dried pyridine was added to the residue and the mixture was cooled down with ice. And 1.50 g of trans-4-guanidinomethyl cyclohexane carboxylic acid·hydrochloride was added to the cooled mixture. After stirring this mixture during night cooling down with water, the mixture was concentrated under reduced pressure. After acetone was added to the residue, precipitated crystals were collected by filtration, and they were washed with acetone. The crude crystals 2.85 g were obtained. The crude crystals were dispersed into isopropanol, collected by filtration, and washed with isopropanol. 2.44 g of trans-4-guanidinomethyl cyclohexane carboxylic acid[4-(4-cyclohexylmethyloxy carbonylphenyl)phenylester]·hydrochloride was obtained.

mp 192–196° C.; NMR (DMSO-$d_6$) δ 0.5–3.3 (12H,m), 4.10 (2H,d), 6.9–8.5 (13H,m)

The value of MIC against *bacillus subcillus* ATCC 6633 measured in accordance with the standard method of Japanese Chemotherapy Academy was 25 g/ml.

EXAMPLE 24

Cooling down with ice, 0.30 g of thionyl chloride was added by dropping to a mixture of 4-(3-bromo-4-hydroxyphenyl)benzoate(4-methyl benzylester) 2.00 g, dried pyridine 0.40 g and dried tetrahydrofuran 10 ml. After the mixture was stirred for 3 hours at room temperature, precipitated crystals were collected by filtration. The filtrate was concentrated under reduced pressure. 10 ml of dried pyridine was added to the residue and the mixture was cooled down with ice. And 0.54 g of trans-4-guanidinomethyl cyclohexane carboxylic acid·hydrochloride was added to the cooled mixture. After stirring this mixture during night at room temperature, the mixture was concentrated under reduced pressure. After acetone was added to the residue, precipitated crystals were collected by filtration, and they were washed with acetone. 0.79 g of crude crystals were obtained. The crude crystals were dispersed into isopropanol, collected by filtration, and washed with isopropanol. 0.60 g of trans-4-guanidinomethyl cyclohexane carboxylic acid [2-bromo-4-[4-(4-methylbenzyloxycarbonyl)phenyl]phenylester]·hydrochloride was obtained.

mp 135–138° C.; NMR (DMSO-$d_6$) δ 0.6–3.3 (12H,m), 2.33 (3H,s), 5.33 (2H,s), 6.4–8.6 (16H,m)

The value of MIC against *bacillus subcillus* ATCC 6633 measured in accordance with the standard method of Japanese Chemotherapy Academy was >25 g/ml.

EXAMPLE 25

Cooling down with ice, 0.56 g of thionyl chloride was added by dropping to a mixture of 4-(4-hydroxyphenyl) benzoate(2,4-dimethyl benzylester) 3.10 g, dried pyridine 0.74 g and dried tetrahydrofuran 15 ml. After the mixture was stirred for 3 hours at room temperature, precipitated crystals were collected by filtration. The filtrate was concentrated under reduced pressure. 15 ml of dried pyridine was added to the residue and the mixture was cooled down with ice. And 1.00 g of trans-4-guanidinomethyl cyclohexane carboxylic acid·hydrochloride was added to the cooled mixture. After stirring this mixture during night cooling down with water, the mixture was concentrated under reduced pressure. After acetone was added to the residue, precipitated crystals were collected by filtration, and they were washed with acetone. The crude crystals were dispersed into isopropanol, collected by filtration, and washed with isopropanol. 1.48 g of trans-4-guanidinomethyl cyclohexane carboxylic acid [4-[4-(2,4-dimethyl benzyloxycarbonyl)phenyl]phenylester]·hydrochloride was obtained.

mp 177–180° C.; NMR (DMSO-$d_6$) δ 0.6–3.3 (18H,m), 5.31 (2H,s), 6.5–8.5 (16H,m)

The value of MIC against *bacillus subcillus* ATCC 6633 measured in accordance with the standard method of Japanese Chemotherapy Academy was >25 g/ml.

EXAMPLE 26

Cooling down with ice, 0.19 g of thionyl chloride was added by dropping to a mixture of 4-(4-hydroxyphenyl) benzoate(2-phenylethylester) 1.01 g, dried pyridine 0.25 g and dried tetrahydrofuran 10 ml. After the mixture was stirred for 3 hours at room temperature, precipitated crystals were collected by filtration. The filtrate was concentrated under reduced pressure. 10 ml of dried pyridine was added to the residue and the mixture was cooled down with ice. And 0.34 g of trans-4-guanidinomethyl cyclohexane carboxylic acid·hydrochloride was added to the cooled mixture. After stirring this mixture during night cooling down with water, precipitated crystals were collected by filtration, and they were washed with acetone. The crude crystals were obtained. The crude crystals were dispersed into acetone, collected by filtration, and washed with acetone. 0.33 g of trans-4-guanidinomethyl cyclohexane carboxylic acid [4-[4-(2-phenylethyloxycarbonyl)phenyl]phenylester]·hydrochloride was obtained.

mp 192–194° C.; NMR (DMSO-$d_6$) δ 0.7–3.3 (14H,m), 4.49 (2H,t), 6.7–8.4 (18H,m)

The value of MIC against *bacillus subcillus* ATCC 6633 measured in accordance with the standard method of Japanese Chemotherapy Academy was >25 g/ml.

EXAMPLE 27

Cooling down with ice, 0.09 g of thionyl chloride was added by dropping to a mixture of 4-(4-fluorophenyl)phenol 0.28 g, dried pyridine 0.12 g and dried tetrahydrofuran 5 ml. After the mixture was stirred for 3 hours at room temperature, precipitated crystals were collected by filtration. The filtrate was concentrated under reduced pressure. 5 ml of dried pyridine was added to the residue and cooled down with ice. 0.16 g of trans-4-guanidinomethyl cyclohexane carboxylic acid was added to the cooled mixture. After the mixture was stirred during night cooling down with water, the mixture was concentrated under reduced pressure and acetone was added to the residue. Precipitated crystals were collected by filtration. And the precipitated crystals were washed with acetone and crude crystals were obtained. The crude crystals were dispersed into isopropanol, collected by filtration, and washed with isopropanol. 0.10 g of trans-4-guanidinomethyl cyclohexane carboxylic acid [4-(4-fluorophenyl)phenylester]·hydrochloride was obtained.

mp 193–197° C.; NMR (DMSO-$d_6$) δ 0.8–3.3 (12H,m), 6.6–8.1 (13H,m)

EXAMPLE 28

Cooling down with ice, 0.50 g of trans-4-guanidinomethyl cyclohexane carboxylic acid [4-(4- benzyloxycarbonylphenyl)phenylester.hydrochloride which was obtained in Example 3 was suspended in water 20 ml, and was added with 0.20 g of potassium hydrogen carbonate. The mixture was stirred for 3 hours cooling down with ice and then refrigerated during night. Precipitated crystals were collected by filtration and were washed in order with water and acetone. 0.47 g of carbonate was obtained. The carbonate was added in portions to 30 ml of acetic acid, and made hydrogen addition under existence of 0.05 g of 10% Pd—C (involved 48.3% water) at normal temperature and normal pressure. After water 20 ml, N,N-dimethylformamide 20 ml and methanesulfonic acid 0.09 g were in order added, a catalyst was removed by filtration. The solution was concentrated under reduced pressure, and acetone was added to the residue. The precipitated crystals were collected by filtration, washed in order with acetone and hexane. 0.37 g of 4-[4-(trans-4-guanidinomethyl cyclohexylcarbonyloxy)phenyl]benzoate·methansulfonate was obtained.

mp 256–258° C.; NMR (DMSO-$d_6$) δ 0.7–3.2 (12H,m), 2.48 (3H,s), 6.6–8.2 (14H,m)

The value of MIC against *bacillus subcillus* ATCC 6633 and *Escherichia coli*. NHJC-2 measured in accordance with the standard method of Japanese Chemotherapy Academy was >25 g/ml.

EXAMPLE 29

Cooling down with ice, 0.41 g of thionyl chloride was added by dropping to a mixture of 6-hydroxy-2-naphthoic acid ethylester 1.50 g, pyridine 0.55 g and dried tetrahydrofuran 30 ml. After the mixture was stirred for 4 hours at room temperature, precipitated crystals were collected by filtration. The filtrate was concentrated under reduced pressure and crystals were obtained. 30 ml of dried pyridine was added to the crystals and the mixture was cooled down with ice. And 0.74 g of trans-4-guanidinomethyl cyclohexane carboxylic acid·hydrochloride was added to the cooled mixture in portions. After stirring this mixture overnight at room temperature, the mixture was concentrated under reduced pressure. Acetone was wadded to the residue and precipitated crystals were collected by filtration, and they were washed with acetone. 1.03 g of trans-4-guanidinomethyl cyclohexane carboxylic acid (2,4-dichloro-1-naphthylester)·hydrochloride was obtained.

mp 196–200° C.; NMR (DMSO-$d_6$) δ 0.8–3.3 (12H,m), 1.40 (3H,t), 4.38 (2H,q), 7.0–8.8 (11H,m)

EXAMPLE 30

Trans-4-guanidinomethyl cyclohexane carboxylic acid·hydrochloride 2.00 g was suspended in dried pyridine 30 ml, and added with 2,4-dichloro-1-naphthol 1.99 g and N,N'-dicyclohexylcarbodiimido 1.93 g. The mixture was stirred for 4 hours at 40° C. After cooling down with water, precipitated crystals were collected by filtration. The obtained crude crystals were suspended in chloroform three times repeatedly. 2.99 g of trans-4-guanidinomethyl cyclohexane carboxylic acid (2,4-dichloro-1-naphthyleter)·hydrochloride was obtained.

mp 208–209° C.; NMR (DMSO-$d_6$) δ 0.6–3.3 (12H,m), 7.30 (4H,bs), 7.5–8.4 (6H,m)

EXAMPLE 31

Cooling down with ice, 1.11 g of thionyl chloride was added by dropping to a mixture of 6-bromo-2-naphthol 4.16 g, dried pyridine 1.48 g and dried tetrahydrofuran 30 ml. After the mixture was stirred for 3 hours cooling down with ice, precipitated crystals were collected by filtration. The filtrate was concentrated under reduced pressure. 30 ml of dried pyridine was added to the residue and the mixture was homogenized cooling down with ice. And 2.00 g of trans-4-guanidinomethyl cyclohexane carboxylic acid·hydrochloride was added to the cooled mixture in portions. After stirring this mixture during night at room temperature, precipitated crystals were collected by filtration, and they were washed with acetone. 0.90 g of trans-4-guanidinomethyl cyclohexane carboxylic acid(6-bromo-2-naphthyl ester)·hydrochloride was obtained.

mp 185–186.5° C.; NMR (DMSO-$d_6$) δ 0.5–3.3 (12H,m), 6.7–8.5 (11H,m)

EXAMPLE 32

Cooling down with ice, 1.67 g of thionyl chloride was added by dropping to a mixture of 4-cyclohexyphenol 4.94 g, pyridine 2.21 g and dried tetrahydrofuran 30 ml. After the mixture was stirred for 4 hours at room temperature, precipitated crystals were collected by filtration. The filtrate was concentrated under reduced pressure and an oily product was obtained. 30 ml of dried pyridine was added to the oily product and cooled down with ice. And 3.00 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed with acetone. 4.52 g of trans-4-guanidinomethyl cyclohexane carboxylic acid(4-cyclohexyphenylester)·hydrochloride was obtained.

mp 205–206° C.; NMR (DMSO-$d_6$) δ 0.8–3.3 (23H,m), 6.91 (2H,d), 7.17 (2H,d), 7.23 (4H,bs), 7.91 (1H,bt)

EXAMPLE 33

Cooling down with ice, 1.67 g of thionyl chloride was added by dropping to a mixture of 4-benzylphenol 5.16 g, pyridine 2.21 g and dried tetrahydrofuran 30 ml. After the mixture was stirred for 4 hours at room temperature, precipitated crystals were collected by filtration. The filtrate was concentrated under reduced pressure and an oily product was obtained. 30 ml of dried pyridine was added to the oily product and cooled down with ice. And 3.00 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed with acetone. 4.74 g of crude crystals were obtained and the crystals were recrystallized with 28 ml of 2-propanol. 4.23 g of trans-4-guanidinomethyl cyclohexane carboxylic acid (4-benzylphenylester)·hydrochloride was obtained.

mp 142–143° C.; NMR (DMSO-$d_6$) δ 0.8–3.3 (12H,m), 3.90 (2H,s), 6.8–7.5 (13H,m), 7.93 (1H,bt)

EXAMPLE 34

Cooling down with ice, 1.67 g of thionyl chloride was added by dropping to a mixture of 4-(1-methyl-1-phenylethyl)phenol 5.94 g, pyridine 2.21 g and dried tetrahydrofuran 30 ml. After the mixture was stirred for 4 hours at room temperature, precipitated crystals were collected by filtration. The filtrate was concentrated under reduced pressure and an oily product was obtained. 30 ml of dried pyridine was added to the oily product and cooled down with ice. And 3.00 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed with acetone. 4.92 g of trans-4-guanidinomethyl cyclohexane carboxylic acid [4-(1-methyl-1-phenylethyl)phenylester]·hydrochloride was obtained.

mp 150–151° C.; NMR (DMSO-$d_6$) δ 0.7–3.3 (12H,m), 1.63 (6H,s), 6.89 (2H,d), 7.0–7.4 (11H,m), 7.87 (1H,bt)

EXAMPLE 35

Cooling down with ice, 1.67 g of thionyl chloride was added by dropping to a mixture of 4-phenoxyphenol 5.21 g, pyridine 2.21 g and dried tetrahydrofuran 30 ml. After the mixture was stirred for 4 hours at room temperature, precipitated crystals were collected by filtration. The filtrate was concentrated under reduced pressure and an oily product was obtained. 30 ml of dried pyridine was added to the oily product and cooled down with ice. And 3.00 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed with acetone. 4.78 g of trans-4-guanidinomethyl cyclohexane carboxylic acid(4-phenoxyphenylester)·hydrochloride was obtained.

mp 146–149° C.; NMR (DMSO-$d_6$) δ 0.8–3.3 (12H,m), 6.7–7.7 (13H,m), 7.93 (1H,bt)

EXAMPLE 36

Cooling down with ice, 1.18 g of thionyl chloride was added by dropping to a mixture of 4-(4-hydroxyphenyloxy) benzoate ethylester 5.13 g, pyridine 1.57 g and dried tetrahydrofuran 30 ml. After the mixture was stirred for 4 hours at room temperature, precipitated crystals were collected by filtration. The filtrate was concentrated under reduced pressure and an oily product was obtained. 30 ml of dried pyridine was added to the oily product and cooled down with ice. And 1.95 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed in order with acetone and hexane. 2.95 g of trans-4-guanidinomethyl cyclohexane carboxylic acid [4-(4-ethoxycarbonyl phenyloxy)phenylester]·hydrochloride was obtained.

mp 137–140° C.; NMR (DMSO-$d_6$) δ 1.33 (3H,t), 0.8–3.3 (12H,m), 4.31 (2H,q), 7.04 (2H,d), 7.14 (4H,s), 7.28 (4H, bs), 7.98 (2H,d), 8.00 (1H,bs)

EXAMPLE 37

Cooling down with ice, 1.67 g of thionyl chloride was added by dropping to a mixture of 4-benzyloxyphenol 5.61 g, pyridine 2.21 g and dried tetrahydrofuran 30 ml. After the mixture was stirred for 4 hours at room temperature, precipitated crystals were collected by filtration. The filtrate was concentrated under reduced pressure and crystals were obtained. 30 ml of dried pyridine was added to the crystals and the mixture was cooled down with ice. And 3.00 g of trans-4-guanidinomethyl cyclohexane carboxylic acid·hydrochloride was added to the cooled mixture in portions. After stirring this mixture during night at room temperature, the mixture was concentrated under reduced pressure and acetone added to the residue. Precipitated crystals were collected by filtration, and they were washed with acetone. 4.76 g of trans-4-guanidinomethyl cyclohexane carboxylic acid(4-benzyloxyphenylester)·hydrochloride was obtained.

mp 211–212° C.; NMR (DMSO-$d_6$) δ 0.8–3.3 (12H,m), 5.07 (2H,s), 6.99 (4H,s), 7.27 (4H,bs), 7.40 (5H,s), 7.94 (1H,bt)

EXAMPLE 38

Cooling down with ice, 1.67 g of thionyl chloride was added by dropping to a mixture of 4-styrylphenol 5.50 g, pyridine 2.21 g and dried tetrahydrofuran 30 ml. After the mixture was stirred for 6 hours at room temperature, precipitated crystals were collected by filtration. The filtrate was concentrated under reduced pressure and crystals were obtained. 80 ml of dried pyridine was added to the crystals and the mixture was cooled down with ice. And 3.00 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed with acetone. 4.89 g of trans-4-guanidinomethyl cyclohexane carboxylic acid(4-styrylphenylester)·hydrochloride was obtained.

mp 213–216° C.; NMR (DMSO-$d_6$) δ 0.7–3.3 (12H,m), 6.7–8.2 (16H,m)

EXAMPLE 39

Cooling down with ice, 0.61 g of thionyl chloride was added by dropping to a mixture of 4-(4-hydroxyphenyl) benzoate(3-phenylpropylester) 3.41 g, pyridine 0.81 g and dried tetrahydrofuran 50 ml. After the mixture was stirred for 3 hours at room temperature, precipitated crystals were collected by filtration. The filtrate was concentrated under reduced pressure and an oily product was obtained. 30 ml of dried pyridine was added to the oily product and cooled down with ice. And 1.10 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration, and they were washed with acetone. The obtained crystals were suspended in 30 ml of 2-propanol, collected by filtration, and washed in order with 2-propanol and acetone. 1.75 g of trans-4-guanidinomethyl cyclohexane carboxylic acid[4-[4-(3-phenylpropyloxycarbonyl)phenyl]phenylester] ·hydrochloride was obtained.

mp 180–185° C.; NMR (DMSO-$d_6$) δ 0.8–3.3 (16H,m), 4.30 (2H,t), 6.8–9.0 (18H,m)

EXAMPLE 40

Cooling down with ice, 0.56 g of thionyl chloride was added by dropping to a mixture of 4-(4-hydroxyphenyl) benzoate[3-(4-fluorophenyloxy)propylester] 3.27 g, pyridine 0.74 g and dried tetrahydrofuran 50 ml. After the mixture was stirred for 3 hours at room temperature, precipitated crystals were collected by filtration. The filtrate was concentrated under reduced pressure and white colored crystals were obtained. 30 ml of dried pyridine was added to the white colored crystals and the mixture was cooled down with ice. And 1.00 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration, and they were washed with acetone. The obtained crystals were suspended in 30 ml of 2-propanol, collected by filtration, and washed in order with 2-propanol and acetone. 1.59 g of trans-4-guanidinomethyl cyclohexane carboxylic acid [4-[4-[3-(4-fluoro phenyloxy)propyloxycarbonyl]phenyl]phenylester]·hydrochloride was obtained.

mp 175–183° C.; NMR (DMSO-$d_6$) δ 0.8–3.3 (14H,m), 4.21 (2H,t), 4.47 (2H,t), 6.8–8.7 (17H,m)

EXAMPLE 41

Cooling down with ice, 0.56 g of thionyl chloride was added by dropping to a mixture of 4-(4-hydroxyphenyl)benzoate(2-cyclohexyl ethylester) 3.03 g, pyridine 0.74 g and dried tetrahydrofuran 50 ml. After the mixture was stirred for 3 hours at room temperature, precipitated crystals were collected by filtration. The filtrate was concentrated under reduced pressure and an oily product was obtained. 30 ml of dried pyridine was added to the oily product and cooled down with ice. And 1.00 g of trans-4-guanidinomethyl cyclohexane carboxylic acid·hydrochloride was added to the cooled mixture. After stirring this mixture during night at room temperature, precipitated crystals were collected by filtration, and they were washed in order with pyridine and acetone. The obtained crystals were suspended in 30 ml of 2-propanol, collected by filtration, and washed in order with 2-propanol and acetone. 1.77 g of trans-4-guanidinomethyl cyclohexane carboxylic acid[4-[4-(2-cyclohexyl oxycarbonyl)phenyl]phenylester]·hydrochloride was obtained.

mp 192–205° C.; NMR (DMSO-$d_6$) δ 0.7–3.3 (25H,m), 4.31 (2H,t), 6.9–9.0 (13H,m)

EXAMPLE 42

Cooling down with ice, 0.28 g of thionyl chloride was added by dropping to a mixture of 4-(4-hydroxyphenyl)benzoate(trans-4-n-butyl cyclohexylmethylester) 1.71 g, pyridine 0.37 g and dried tetrahydrofuran 30 ml. After the mixture was stirred for 3 hours at room temperature, precipitated crystals were collected by filtration. The filtrate was concentrated under reduced pressure and an oily product was obtained. 30 ml of dried pyridine was added to the oily product and cooled down with ice. And 0.50 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration, and they were washed with acetone. The obtained crystals were suspended in 30 ml of 2-propanol, collected by filtration, and washed in order with 2-propanol and acetone. 0.43 g of trans-4-guanidinomethyl cyclohexane carboxylic acid [4-[4-(trans-4-n-butylcyclohexylmethyloxycarbonyl)phenyl]phenylester]·hydrochloride was obtained.

mp 191–196° C.; NMR (DMSO-$d_6$) δ 0.4–3.3 (31H,m), 3.9–4.4 (2H,m), 6.9–8.7 (13H,m)

EXAMPLE 43

Cooling down with ice, 5.55 g of thionyl chloride was added by dropping to a mixture of 4-(4-hydroxyphenyl)benzoate(2-methylbenzylester) 29.72 g, pyridine 7.38 g and dried tetrahydrofuran 150 ml. After the mixture was stirred for 4 hours at room temperature, precipitated crystals were collected by filtration. The filtrate was concentrated under reduced pressure and an oily product was obtained. 80 ml of dried pyridine was added to the oily product and cooled down with ice. And 10.0 g of trans-4-guanidinomethyl cyclohexane carboxylic acid·hydrochloride was added to the cooled mixture in portions. After stirring this mixture during night at room temperature, the mixture was concentrated under reduced pressure and acetone was added to the residue. Precipitated crystals were collected by filtration, and they were washed with acetone. 22.43 g of trans-4-guanidinomethyl cyclohexane carboxylic acid [4-[4-(2-methylbenzyloxy carbonyl)phenyl]phenylester]·hydrochloride was obtained.

mp 191–194° C.; NMR (DMSO-$d_6$) δ 0.8–3.3 (12H,m), 2.39 (3H,s), 5.32 (2H,s), 6.9–8.2 (17H,m)

EXAMPLE 44

Cooling down with ice, 2.22 g of thionyl chloride was added by dropping to a mixture of 4-(4-hydroxyphenyl)benzoate(3-methylbenzylester) 11.89 g, pyridine 2.95 g and dried tetrahydrofuran 100 ml. After the mixture was stirred for 4.5 hours at room temperature, precipitated crystals were collected by filtration. The filtrate was concentrated under reduced pressure and white colored crystals were obtained. 30 ml of dried pyridine was added to the white colored crystals and the mixture was cooled down with ice. And 4.00 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration, and they were washed with acetone. 8.62 g of trans-4-guanidinomethyl cyclohexane carboxylic acid [4-[4-(3-methylbenzyloxycarbonyl)phenyl]phenylester]·hydrochloride was obtained.

mp 178–180° C.; NMR (DMSO-$d_6$) δ 0.8–3.3 (12H,m), 2.33 (3H,s), 5.30 (2H,s), 6.9–8.3 (17H,m)

EXAMPLE 45

Cooling down with ice, 1.18 g of thionyl chloride was added by dropping to a mixture of 4-(4-hydroxyphenyl)benzoate[2-(4-chloro phenyl)ethylester] 7.00 g, pyridine 1.57 g and dried tetrahydrofuran 100 ml. After the mixture was stirred for 3 hours at room temperature, precipitated crystals were collected by filtration. The filtrate was concentrated under reduced pressure and crystals were obtained. 40 ml of dried pyridine and 30 ml of N,N-dimethylformamido were added to the crystals and cooled down with ice. And 2.13 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration, and they were washed with acetone. The obtained crystals were suspended in 30 ml of 2-propanol, collected by filtration, and washed in order with 2-propanol and acetone. 3.84 g of trans-4-guanidinomethyl cyclohexane carboxylic acid [4-[4-[2-(4-chlorophenyl)ethyloxycarbonyl)phenyl]phenylester]·hydrochloride was obtained.

mp 195–202° C.; NMR (DMSO-$d_6$) δ 0.8–3.3 (14H,m), 4.47 (2H,t), 6.8–8.2 (17H,m)

EXAMPLE 46

Cooling down with ice, 1.25 g of thionyl chloride was added by dropping to a mixture of 4-(4-hydroxyphenyl) benzoate[2-(4-methyl phenyl)ethylester] 7.00 g, pyridine 1.67 g and dried tetrahydrofuran 100 ml. After the mixture was stirred for 3 hours at room temperature, precipitated crystals were collected by filtration. The filtrate was concentrated under reduced pressure and crystals were obtained. 40 ml of dried pyridine and 30 ml of N,N-dimethylformamido were added to the crystals and cooled down with ice. And 2.26 g of trans-4-guanidinomethyl cyclohexane carboxylic acid·hydrochloride was added to the cooled mixture. After stirring this mixture during night at room temperature, the mixture was concentrated under reduced pressure and acetone was added to the residue. Precipitated crystals were collected by filtration, and they were washed with acetone. The obtained crystals were suspended in 30 ml of 2-propanol, collected by filtration, and washed in order with 2-propanol and acetone. 2.96 g of trans-4-guanidinomethyl cyclohexane carboxylic acid [4-[4-[2-(4-methylphenyl)ethyloxycarbonyl)phenyl]phenylester] ·hydrochloride was obtained.

mp 182–190° C.; NMR (DMSO-$d_6$) δ 0.8–3.3 (14H,m), 2.23 (3H,s), 4.43 (2H,t), 6.8–8.1 (17H,m)

EXAMPLE 47

25 ml of N,N-dimethylformamido was added to 5.00 g of trans-4-guanidinomethyl cyclohexane carboxylic acid[4-[4-(4-methyl benzyloxycarbonyl)phenyl]phenylester] ·hydrochloride, and solution of potassium bicarbonate 2.08 g and water 10 ml was added by dropping to the mixture cooling down with ice. After stirring the mixture during night cooling down with ice, precipitated crystals were collected by filtration and washed in order with water and acetone. 5.01 g of trans-4-guanidinomethyl cyclohexane carboxylic acid [4-[4-(4-methyl benzyloxycarbonyl)phenyl]phenylester]·carbonate was obtained.

mp 110–120° C. (decomposition)

EXAMPLE 48

5.00 g of trans-4-guanidinomethyl cyclohexane carboxylic acid [4-[4-(4-methylbenzyloxycarbonyl)phenyl]phenylester]·carbonate was suspended in 30 ml of acetone, and 0.91 g of methanesulfonic acid was added by dropping to the mixture cooling down with ice. After stirring the mixture during night at room temperature, precipitated crystals were collected by filtration and washed with acetone. Crude crystals were obtained and recrystallized with acetone involving water. 4.27 g of [4-[4-(4-methyl benzyloxycarbonyl)phenyl]phenylester]·methansulfonate was obtained.

mp 187–191° C.; NMR (DMSO-$d_6$) δ 0.8–3.3 (12H,m), 2.30 (3H,s), 2.45 (3H,s), 5.32 (2H,s), 6.8–8.3 (17H,m)

EXAMPLE 49

3.00 g of trans-4-guanidinomethyl cyclohexane carboxylic acid [4-[4-(4-methylbenzyloxycarbonyl)phenyl]phenylester]·carbonate was suspended in 30 ml of methanol, and 1.07 g of p-toluenesulfonic acid·1 hydrate was added by dropping to the mixture cooling down with ice. After stirring the mixture during night at room temperature, 100 ml of chloroform was added to the mixture. Some insoluble substances were removed by filtration. The filtrate was concentrated under reduced pressure and acetone was added to the residue. Precipitated crystals were collected by filtration and washed with acetone. 2.98 g of [4-[4-(4-methylbenzyloxycarbonyl)phenyl]phenylester]·p-toluenesulfonate was obtained.

mp 215–216.5° C.; NMR (DMSO-$d_6$) δ 0.7–3.3 (12H,m), 2.27 (6H,s), 5.28 (2H,s), 6.8–8.3 (21H,m)

EXAMPLE 50

3.00 g of trans-4-guanidinomethyl cyclohexane carboxylic acid [4-[4-(4-methylbenzyloxycarbonyl)phenyl]phenylester]·carbonate was suspended in 50 ml of methanol, and 0.34 g of acetic acid was added by dropping to the mixture cooling down with ice. After stirring the mixture during night at room temperature, some insoluble substances were removed by filtration. The filtrate was concentrated under reduced pressure and acetone was added to the residue. Precipitated crystals were collected by filtration and washed with acetone. 2.82 g of [4-[4-(4-methylbenzyloxycarbonyl)phenyl]phenylester]·acetate was obtained.

mp 146–150° C.; NMR (DMSO-$d_6$) δ 0.7–3.3 (12H,m), 1.68 (3H,s), 2.27 (3H,s), 5.26 (2H,s), 6.9–8.5 (17H,m)

EXAMPLE 51

50 ml of methanol was added to 0.65 g of fumaric acid, and 3.00 g of trans-4-guanidinomethyl cyclohexane carboxylic acid[4-[4-(4-methyl benzyloxycarbonyl)phenyl]phenylester]·carbonate was added in portions to the mixture cooling down with ice. After stirring the mixture during night at room temperature, 100 ml of chloroform was added to the mixture and some insoluble substances were removed by filtration. The filtrate was concentrated under reduced pressure and acetone was added to the residue. Precipitated crystals were collected by filtration and washed with acetone. 3.23 g of crude crystals were obtained. 50 ml of ethanol was added to the crystals, and the mixture was stirred for 1 hour at room temperature. Crystals were collected by filtration and washed in order with ethanol and acetone. 2.61 g of [4-[4-(4-methylbenzyloxycarbonyl)phenyl]phenylester]·fumarate was obtained.

mp 185–190° C.; NMR (DMSO-$d_6$) δ 0.7–3.3 (12H,m), 2.28 (6H,s), 5.28 (2H,s), 6.0–8.3 (19H,m), 8.68 (1H,bs)

EXAMPLE 52

30 ml of methanol was added to 1.19 g of citric acid·1 hydrate, and 3.00 g of trans-4-guanidinomethyl cyclohexane carboxylic acid [4-[4-(4-methylbenzyloxycarbonyl)phenyl]phenylester]·carbonate was added in portions to the mixture cooling down with ice. After stirring the mixture during night at room temperature, precipitated crystals were collected by filtration and washed in order with methanol and acetone. 2.74 g of [4-[4-(4-methylbenzyloxycarbonyl)phenyl]phenylester]·½ citrate was obtained.

mp 187–190° C. (decomposition)

The raw compounds of Examples, which were shown as Formula (III), were prepared as follows.

Sample 1

At room temperature, 0.7 ml of concentrated sulfuric acid was added to 5.00 g of 4-(4-hydroxyphenyl)benzoic acid suspended in 50 ml of ethanol. After the mixture was refluxed with heating for 7 hours, the mixture was concentrated under reduced pressure. Water and ethyl acetate were added to the residue, and then the organic layer was washed in order with water, saturated sodium hydrogen carbonate and saturated sodium chloride solution. And it was dried with anhydrous magnesium sulfate, and concentrated under reduced pressure. Obtained crude crystals were purified by silica gel column chromatography with toluene-ethyl acetate eluent. Obtained crystals were dispersed by hexane and collected by filtration and washed with hexane. 4-(4-hydroxyphenyl)benzoate ethylester 5.04 g was obtained.
mp 156–157° C.

Sample 2

2.25 g of methanol solution including 28% sodium methylate was added to 2.50 g of 4-(4-hydroxyphenyl) benzoic acid suspended in 10 ml of methanol. After the mixture was stirred for 5 minutes, it was concentrated under reduced pressure. 10 ml of N,N-dimethylformamido and 2.43 g of benzyl-bromoamide were added to the residue. The mixture was stirred during night at room temperature and poured into 30 ml of ice water, and extracted with 50 ml of toluene. The organic layer was washed with in order saturated sodium hydrogen and water, dried with anhydrous magnesium sulfate, and concentrated under reduced pressure. Obtained crude crystals were purified by silica gel column chromatography with toluene-ethyl acetate eluent, and hexane was added to them. Precipitated crystals were collected by filtration, and washed with hexane. 4-(4-hydroxyphenyl)benzoate benzylester 2.60 g was obtained.
mp 131–133° C.

In accordance with the sample procedures as above described the compounds shown as Formula (III) in Examples 9, 10, 14–21, 23, 25 and 26 were prepared. The prepared compounds and the physical properties thereof were described as follows respectively.

3-phenylsalicylic acid benzylester: mp 69–70° C.
3-phenylsalicylic acid(4-fluorobenzylester): mp 85–86° C.
4-(4-hydroxyphenyl)benzoate(4-methylbenzylester): mp 128–130° C.
4-(4-hydroxyphenyl)benzoate(4-chlorobenzylester): mp 138–140° C.
4-(4-hydroxyphenyl)benzoate(4-fluorobenzylester): mp 157–158° C.
4-(4-hydroxyphenyl)benzoate(4-t-butylbenzylester): mp 125–126° C.
4-(4-hydroxyphenyl)benzoate(4-methoxybenzylester): mp 156–159° C.
4-(4-hydroxyphenyl)benzoate(2-fluorobenzylester): mp 154–155° C.
4-(4-hydroxyphenyl)benzoate isopropylester: mp 118–120° C.
4-(4-hydroxyphenyl)benzoate(4-trifluoromethyl-benzylester): mp 141–142° C.
4-(4-hydroxyphenyl)benzoate cyclohexylmethylester: mp 172–176° C.
4-(4-hydroxyphenyl)benzoate(2,4-dimethylbenzylester): mp 139–145° C.
4-(4-hydroxyphenyl)benzoate(2-phenylethylester): mp 152–155° C.

The raw compounds of Examples 39–46 were prepared by the same procedures as above mentioned or by the procedures applied above. The prepared compounds and the physical properties thereof were described as follows.

4-(4-hydroxyphenyl)benzoate(3-phenylpropylester): mp 98–99° C.
4-(4-hydroxyphenyl)benzoate[3-(4-fluorophenyloxy) propylester]: mp 151–153° C.
4-(4-hydroxyphenyl)benzoate(2-cyclohexylethylester): mp 133–134° C.
4-(4-hydroxyphenyl)benzoate(trans-4-n-butylcyclo-hexylmethylester): mp 130–131° C.
4-(4-hydroxyphenyl)benzoate(2-methylbenzylester): mp 148–150° C.
4-(4-hydroxyphenyl)benzoate(3-methylbenzylester): mp 98.5–99.5° C.
4-(4-hydroxyphenyl)benzoate[2-(4-chlorophenyl) ethylester]: mp 177–180° C.
4-(4-hydroxyphenyl)benzoate[2-(4-methylphenyl) ethylester]: mp 180–182° C.

Sample 3

N-bromosuccinimide 1.98 g was added to a mixture of 3-phenylsalicylic acid (4-fluorobenzylester) 3.26 g and N,N-dimethylformamido 15 ml. After the mixture was stirred during night at room temperature, the mixture was poured into ice water and extracted with toluene. The organic layer was washed with water, dried with anhydrous magnesium sulfate, and concentrated under reduced pressure. The residue was purified by silica gel column chromatography with toluene-ethyl acetate eluent, and hexane was added to them. Precipitated crystals were collected by filtration, and washed with hexane. 5-bromo-3-phenylsalicylate(4-fluorobenzylester) 3.64 g was obtained.
mp 87–88° C.

Sample 4

N-chlorosuccinimide 15.35 g was added to a mixture of 2-phenylphenol 9.32 g and N,N-dimethylformamido 50 ml and the mixture was stirred for 3.5 hours at 60° C. After cooling down with water, toluene was added to the mixture, poured into ice water and separated. The organic layer was washed with water, dried with anhydrous magnesium sulfate, and concentrated under reduced pressure. Hexane was added to the residue, precipitated crystals were collected by filtration, and washed with hexane. 2,4-dichloro-6-phenylphenol 5.86 g was obtained.
mp 52–53° C.

Sample 5

N-chlorosuccinimide 16.47 g was added to a mixture of 4-phenylphenol 10.00 g and N,N-dimethylformamido 50 ml, and the mixture was stirred for 3 hours at 60° C. After cooling down with water, 100 ml of toluene was added to the mixture. The mixture was poured into ice water and separated. The organic layer was washed with water, dried with anhydrous magnesium sulfate, and concentrated under reduced pressure. The residue was purified by silica gel column chromatography with chloroform eluent, and hexane was added to the residue. Precipitated crystals were collected by filtration, and washed with hexane. 2,6-dichloro-4-phenylphenol 2.37 g was obtained.
mp 84–85° C.

Sample 6

Keeping at lower than 35° C. of internal temperature with ice water, N-bromosuccinimide 3.66 g was added to a mixture of 4-(4-hydroxyphenyl)benzoate 4.00 g and N,N-dimethylformamido 50 ml. After the mixture was stirred during night at room temperature, the mixture was poured into ice water and extracted with chloroform. The organic layer was washed with water, dried with anhydrous magnesium sulfate, and concentrated under reduced pressure. Hexane was added to the residue and precipitated crystals were collected by filtration. Crude crystals of 4-(3-bromo-4-hydroxyphenyl)benzoate 4.88 g were obtained. 40 ml of methanol was added to the crude crystals 4.00 g and 2.63 g of methanol solution including 28% sodium methylate was added by dropping to the mixture cooling down with ice. After the mixture was stirred for 1 hour at room temperature, the mixture was concentrated under reduced pressure. 80 ml of N,N-dimethyl formamido and also, cooling down with ice, 2.78 g of 4-methylbenzylbromide was added to the residue. After the mixture was stirred for 3 days at room temperature, the mixture was poured into ice water and extracted with toluene. The organic layer was washed in order with saturated sodium hydrogen carbonate and water, dried with anhydrous magnesium sulfate, and concentrated under reduced pressure. 4.98 g of oily product was obtained. The oily product was purified by silica gel column chromatography with toluene-ethyl acetate eluent, and hexane was added to them. Precipitated crystals were collected by filtration, and washed with hexane. 4-(3-bromo-4-hydroxyphenyl)benzoate (4-methylbenzylester) 2.35 g was obtained.

mp 93–94° C.

Further also, the examples of the preparation method for compounds of the present invention were described as follows.

EXAMPLE 53

| Powder (Pellets): | |
| --- | --- |
| Compound of Example 14 | 200 mg |
| Milk Sugar | a proper quantity |
| Corn Starch | a proper quantity |
| Sucrose Aliphatic Ester | 50 mg |
| Hydroxy Propyl Cellulose | 20 mg |
| Lauryl Sodium Sulfate | a very small quantity |
| | 500 mg |

20% solution of hydroxy propyl cellulose which was annexed with Lauryl Sodium Sulfate as a binding agent was added to a mixed powder of the compound of Example 14, milk sugar, corn starch and sucrose aliphatic ester. The mixture was granulated, dried and molded to adopted to granules. 500 mg/package of granule was prepared.

EXAMPLE 54

| Capsules: | |
| --- | --- |
| Compound of Example 14 | 100 mg |
| D-mannitol | a proper quantity |
| Parial α(alpha)-Starch | 25 mg |
| Calcium Carmelose | 5 mg |
| Magnesium Stearate | 3 mg |
| | 200 mg |

The compound of Example 14 and the above prescribed powders were mixed and 200 ml of the mixed powders was filled in NIKKYOKU CAPSULE size 3.

EXAMPLE 55

| Suspensions: | |
| --- | --- |
| Compound of Example 14 | 100 mg |
| Sodium Alginic Acid | 50 mg |
| Sodium Saccharine | 1 mg |
| Peppermint Oil | a very small quantity |
| 4% ethylparaben solution | 0.1 ml |
| Purified Water | |
| | Adjusted to Total 10 ml |

Sodium alginic acid was added to a part of purified water, rapidly mixed and wetted homogeneously. And then ethylparaben solution and sodium saccharine were dissolved into the rest of purified water. The solution was added to the mixture little by little. Also the compound of Example 14 and peppermint oil were added to it and mixed. Homogeneous suspensions were prepared.

EXAMPLE 56

Granules:

100 mg of trans-4-guanidinomethyl cyclohexane carboxylic acid (6-bromo-2-naphthylester)·hydrochloride, that is the compound of Example 31, 80 ml of milk sugar, 25 ml of corn starch and 30 ml of crystal cellulose were mixed well. Solution including hydroxy propylcellulose 15 ml was added to the mixture. The mixture was kneaded, granulated, dried and classificated and granules were prepared.

TABLE 1

| | M I C ($\mu$g/ml) | | |
| --- | --- | --- | --- |
| Compounds | Objected Strain 1 | Objected Strain 2 | Objected Strain 3 |
| Example 1 | 12.5 | 6.25 | >25 |
| Example 2 | 1.56 | 0.78 | >25 |
| Example 3 | 0.78 | 0.39 | >25 |
| Example 4 | 1.56 | 0.39 | >25 |
| Example 5 | 3.13 | 1.56 | >25 |
| Example 6 | 6.25 | 1.56 | >25 |
| Example 7 | 3.13 | 3.13 | >25 |
| Example 8 | 0.78 | 0.39 | >25 |
| Example 9 | 6.25 | 3.13 | >25 |
| Example 10 | 6.25 | 6.25 | >25 |
| Example 11 | 6.25 | 6.25 | >25 |
| Example 12 | 3.13 | 3.13 | >25 |
| Example 13 | 12.5 | 12.5 | >25 |
| Example 14 | 0.39 | 0.39 | >25 |
| Example 15 | 0.78 | 0.39 | >25 |
| Example 16 | 0.78 | 0.78 | >25 |
| Example 17 | 0.78 | 0.39 | >25 |
| Example 18 | 0.78 | 0.78 | >25 |
| Example 19 | 0.39 | 0.39 | >25 |
| Example 20 | 0.78 | 0.78 | >25 |
| Example 21 | 0.39 | 0.78 | >25 |
| Example 22 | 1.56 | 3.13 | >25 |
| Example 23 | 0.20 | 0.39 | >25 |
| Example 24 | 0.39 | 0.78 | >25 |
| Example 25 | 0.39 | 0.78 | >25 |
| Example 26 | 0.39 | 0.78 | >25 |
| Example 27 | 0.78 | 1.56 | >25 |
| Compound 1 | 3.13 | 0.78 | >25 |
| Compound 2 | 25 | 25 | >25 |
| Ophroxacine | 0.78 | 0.78 | 0.10 |
| Amoxicillin | 0.05 | 0.025 | 6.25 |

Objected Strain 1: *Helicobacter pylori* ATCC 43504
Objected Strain 2: *Helicobacter pylori* ATCC 43629
Objected Strain 3: *Escherichia coli* NIH JC-2

TABLE 2

| | M I C ($\mu$g/ml) | | |
| --- | --- | --- | --- |
| Compounds | Objected Strain 1 | Objected Strain 2 | Objected Strain 3 |
| Example 29 | 6.25 | 12.5 | >25 |
| Example 30 | 3.13 | 3.13 | >25 |
| Example 31 | 3.13 | 0.78 | >25 |
| Compound 3 | >25 | >25 | >25 |
| Compound 4 | 25 | 25 | >25 |

Objected Strain 1: *Helicobacter pylori* ATCC 43504
Objected Strain 2: *Helicobacter pylori* ATCC 43629
Objected Strain 3: *Escherichia coli* NIH JC-2

TABLE 3

| Compounds | MIC (μg/ml) | | |
|---|---|---|---|
| | Objected Strain 1 | Objected Strain 2 | Objected 3 |
| Example 32 | 3.13 | 0.78 | >25 |
| Example 33 | 12.5 | 12.5 | >25 |
| Example 34 | 25 | 25 | >25 |
| Example 35 | 12.5 | 25 | >25 |
| Example 36 | 6.25 | 6.25 | >25 |
| Example 37 | 12.5 | 3.13 | >25 |
| Example 38 | 0.78 | 0.39 | >25 |
| Compound 5 | 12.5 | 6.25 | >25 |
| Compound 6 | 25 | 25 | >25 |
| Compound 7 | 25 | 12.5 | >25 |
| Ophroxacine | 0.78 | 0.78 | 0.10 |
| Amoxicillin | 0.05 | 0.025 | 6.25 |

Objected Strain 1: *Helicobacter pylori* ATCC 43504
Objected Strain 2: *Helicobacter pylori* ATCC 43629
Objected Strain 3: *Escherichia coli* NIH JC-2

TABLE 4

| Compound | MIC (μg/ml) | | | | | | |
|---|---|---|---|---|---|---|---|
| | Strain 4 | Strain 5 | Strain 6 | Strain 7 | Strain 8 | Strain 9 | Strain 10 |
| Compound 1 | 0.39 | 1.56 | 0.39 | 0.78 | | | |
| Example 2 | 0.39 | 1.56 | 0.39 | 0.78 | | | |
| Example 3 | 0.20 | 0.39 | 0.10 | 0.39 | | | |
| Example 8 | 0.10 | 0.39 | 0.10 | 0.39 | 0.20 | 0.39 | 0.39 |
| Example 14 | 0.10 | 0.39 | 0.10 | 0.20 | 0.20 | 0.39 | 0.39 |
| Example 15 | 0.10 | 0.39 | 0.10 | 0.20 | | | |
| Example 16 | 0.20 | 0.78 | 0.20 | 0.39 | | | |
| Example 17 | 0.20 | 0.39 | 0.20 | 0.20 | | | |
| Example 18 | 0.20 | 0.78 | 0.20 | 0.39 | | | |
| Example 19 | 0.20 | 0.78 | 0.20 | 0.39 | | | |
| Example 20 | 0.39 | 1.56 | 0.39 | 0.78 | | | |
| Example 21 | 0.20 | 0.39 | 0.10 | 0.39 | | | |
| Example 23 | 0.20 | 0.39 | 0.20 | 0.39 | | | |
| Example 24 | | 0.39 | 0.20 | 0.39 | | | |
| Example 25 | 0.39 | 0.39 | 0.20 | 0.39 | | | |
| Example 26 | 0.20 | 0.39 | 0.10 | 0.20 | | | |

Strain = Objected Strain
Strain 4: *Helicobacter pylori* No. 1
Strain 5: *Helicobacter pylori* No. 2
Strain 6: *Helicobacter pylori* No. 3
Strain 7: *Helicobacter pylori* No. 4
Strain 8: *Helicobacter pylori* No. 19
Strain 9: *Helicobacter pylori* No. 20
Strain 10: *Helicobacter pylori* No. 28

TABLE 5

| Compound | Objected Strain 1 | | Objected Strain 2 | | Objected Strain 4 | | Objected Strain 5 | | Objected Strain 6 | | Objected Strain 7 | |
|---|---|---|---|---|---|---|---|---|---|---|---|---|
| | MIC | MBC | MIC | MBC | MIC | MBC | MIC | MBC | MIC | MBC | MIC | MBC |
| Example 14 | 0.20 | 0.20 | 0.39 | 1.56 | 0.20 | 0.20 | 0.39 | 1.56 | 0.10 | 0.10 | 0.39 | 0.39 |
| Example 15 | 0.20 | 0.39 | 0.39 | 1.56 | 0.20 | 0.78 | 0.39 | 1.56 | 0.05 | 0.10 | 0.39 | 0.39 |
| Example 16 | 0.20 | 0.39 | 0.39 | 1.56 | 0.20 | 0.78 | 0.78 | 3.13 | 0.05 | 0.10 | 0.10 | 0.39 |

* The unit of MIC and MBC measurements is μg/ml.
* Objected Strain 1: *Helicobacter pylori* ATCC 43504
Objected Strain 2: *Helicobacter pylori* ATCC 43629
Objected Strain 4: *Helicobacter pylori* No. 1
Objected Strain 5: *Helicobacter pylori* No. 2
Objected Strain 6: *Helicobacter pylori* No. 3
Objected Strain 7: *Helicobacter pylori* No. 4

TABLE 6

| Compound | MIC (μg/ml) | | | | | | | | | |
|---|---|---|---|---|---|---|---|---|---|---|
| | Strain 1 | Strain 2 | Strain 3 | Strain 4 | Strain 5 | Strain 6 | Strain 7 | Strain 8 | Strain 9 | Strain 10 |
| Ex. 39 | 0.39 | 0.78 | >25 | 0.39 | 0.78 | 0.20 | 0.39 | | | |
| Ex. 40 | 0.20 | 0.39 | >25 | 0.20 | 0.78 | 0.10 | 0.39 | | | |

TABLE 6-continued

| Compound | MIC (μg/ml) | | | | | | | | | |
|---|---|---|---|---|---|---|---|---|---|---|
| | Strain 1 | Strain 2 | Strain 3 | Strain 4 | Strain 5 | Strain 6 | Strain 7 | Strain 8 | Strain 9 | Strain 10 |
| Ex. 41 | 0.39 | 0.39 | >25 | 0.20 | 0.39 | 0.20 | 0.20 | | | |
| Ex. 42 | 0.39 | 1.56 | >25 | 0.39 | 1.56 | 0.20 | 0.39 | | | |
| Ex. 43 | 0.20 | 0.39 | >25 | 0.20 | 0.20 | 0.20 | 0.78 | 0.10 | 0.39 | 0.39 |
| Ex. 44 | 0.20 | 0.20 | >25 | 0.39 | 0.39 | 0.20 | 0.78 | 0.20 | 0.20 | 0.39 |
| Ex. 45 | 0.39 | 0.39 | >25 | 0.39 | 0.39 | 0.39 | 3.13 | 0.20 | 0.20 | 0.39 |
| Ex. 46 | 0.78 | 0.78 | >25 | 0.39 | 0.39 | 0.20 | 3.13 | 0.39 | 0.20 | 0.39 |
| Ophroxacine | 0.78 | 0.78 | 0.10 | 0.78 | 12.5 | 25.0 | 0.78 | 0.78 | 0.78 | 1.56 |
| Amoxicillin | 0.05 | 0.025 | 6.25 | 0.10 | 0.10 | 0.025 | 0.05 | 0.025 | 0.025 | 0.05 |

\* Strain means Object strain
\* Strain 1: *Helicobacter pylori* ATCC 43504
Strain 2: *Helicobacter pylori* ATCC 43629
Strain 3: *Escherichia coli* NIH JC-2
Strain 4: *Helicobacter pylori* No. 1
Strain 5: *Helicobacter pylori* No. 2
Strain 6: *Helicobacter pylori* No. 3
Strain 7: *Helicobacter pylori* No. 4
Strain 8: *Helicobacter pylori* No. 19
Strain 9: *Helicobacter pylori* No. 20
Strain 10: *Helicobacter pylori* No. 28

TABLE 7

| Compound | MIC (μg/ml) | | | |
|---|---|---|---|---|
| | Strain 11 | Strain 12 | Strain 13 | Strain 14 |
| Example 3 | 3.13 | 6.25 | 25 | 3.13 |
| Example 36 | 6.25 | | 25 | 6.25 |
| Example 8 | 0.78 | 1.56 | 6.25 | 1.56 |
| Example 14 | >25 | >25 | >25 | >25 |
| Example 17 | >25 | >25 | >25 | >25 |
| Example 21 | 25 | >25 | >25 | >25 |
| Example 41 | 25 | >25 | >25 | >25 |
| Example 45 | >25 | >25 | >25 | >25 |
| Ophroxacine | 0.39 | 0.10 | 0.10 | 12.5 |
| Amoxicillin | 0.10 | 0.05 | 0.05 | 0.20 |

\* Strain means Object strain.
\* Strain 11: *Staphylococcus aureus* 209PJC
Strain 12: *Staphylococcus aureus* ATCC 6538
Strain 13: *Bacillus subtilis* ATCC 6633
Strain 14: *Staphylococcus aureus* No. 2 (MRSA)

We claim:

1. A compounds of the general formula VIII:

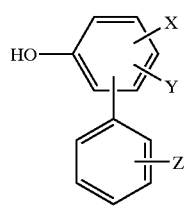

VIII wherein

X is hydrogen or halogen;

Y is hydrogen; and

Z is substituted alkoxycarbonyl having 4–19 carbon atoms wherein a substituent of the alkyl group of the alkoxycarbonyl group is a cycloalkyl group having 3 to 18 carbon atoms.

2. The compound according to claim 1, wherein the Z group is para to the phenol ring.

3. A compounds of the general formula VIII:

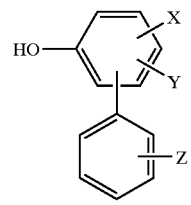

VIII wherein

X is halogen;

Y is hydrogen; and

Z is alkoxycarbonyl having 2–19 carbon atoms wherein the alkoxycarbonyl is substituted with (i) $C_{3-18}$cycloalkyl or (ii) a phenoxy group which is optionally substituted with halogen, $C_{1-10}$alkyl, or $C_{1-10}$alkoxy group.

4. The compound according claim 3, wherein the Z group is para to the phenol ring.

5. A compounds of the general formula VIII:

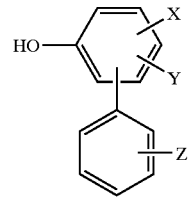

VIII wherein

X is hydrogen;

Y is hydrogen; and

Z is substituted alkoxycarbonyl having 2–19 carbon atoms, wherein the substituent of the alkoxycarbonyl is (i) a $C_{3-18}$cycloalkyl group or (ii) a phenoxy group which is optionally substituted with halogen, $C_{1-10}$alkyl, or $C_{1-10}$alkoxy group.

6. The compound according claim 5, wherein the Z group is para to the phenol ring.

\* \* \* \* \*